US012811003B2

(12) United States Patent
Shelton, IV et al.

(10) Patent No.: US 12,811,003 B2
(45) Date of Patent: Nov. 24, 2026

(54) DYNAMICALLY DETERMINING SURGICAL AUTONOMY LEVEL

(71) Applicant: Cilag GmbH International, Zug (CH)

(72) Inventors: Frederick E. Shelton, IV, Hillsboro, OH (US); Kevin L. Houser, Springboro, OH (US); Taylor W. Aronhalt, Loveland, OH (US); Sarah A. Worthington, Cincinnati, OH (US); Kevin M. Fiebig, Cincinnati, OH (US); Curtis Anthony Maples, Cincinnati, OH (US); Nicholas James Ross, Franklin, OH (US); Shane R. Adams, Lebanon, OH (US); Matthew David Cowperthwait, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 633 days.

(21) Appl. No.: 17/747,693

(22) Filed: May 18, 2022

(65) Prior Publication Data

US 2023/0371950 A1 Nov. 23, 2023

(51) Int. Cl.
*G16H 40/60* (2018.01)
*A61B 34/32* (2016.01)
*A61B 17/072* (2006.01)

(52) U.S. Cl.
CPC ............. *G16H 40/60* (2018.01); *A61B 34/32* (2016.02); *A61B 17/07207* (2013.01); *A61B 2017/07214* (2013.01)

(58) Field of Classification Search
CPC .... A61B 17/07207; A61B 2017/07214; A61B 34/32; A61B 2090/378; G16H 40/60; B25J 9/1689; A61N 1/40
See application file for complete search history.

(56) References Cited

U.S. PATENT DOCUMENTS

| | | | | |
|---|---|---|---|---|
| 5,819,229 | A * | 10/1998 | Boppe .................... | G16H 70/60 600/301 |
| 9,345,481 | B2 | 5/2016 | Hall et al. | |

(Continued)

FOREIGN PATENT DOCUMENTS

| | | | |
|---|---|---|---|
| EP | 1854420 | A1 | 11/2007 |
| EP | 3231373 | A2 | 10/2017 |

(Continued)

OTHER PUBLICATIONS

Kazanzides, P. et al., "Force sensing and control for a surgical robot", Proceedings of the International Conference on Robotics and Automation Nice, France, May 12-14, 1992, pp. 612-617.

(Continued)

*Primary Examiner* — Eric J Yoon
(74) *Attorney, Agent, or Firm* — Condo Roccia Koptiw LLP

(57) ABSTRACT

Systems, methods, and instrumentalities may be described herein for automating a surgical task. The device may receive an indication of a surgical task to be performed with a surgical instrument. Capabilities of the surgical instrument may be associated with levels of automation. The device may monitor a performance of the surgical task with the surgical instrument operating at a first level of automation associated with the levels of automation. The device may detect a trigger event associated with the performance of the surgical task and switch operation of the surgical instrument from the first level of automation to a second level of automation associated with levels of automation, for example, based on the trigger event.

16 Claims, 16 Drawing Sheets

(56) References Cited

U.S. PATENT DOCUMENTS

| | | | | |
|---|---|---|---|---|
| 10,314,644 | B2 | 6/2019 | Brogna | |
| 10,695,081 | B2 | 6/2020 | Shelton, IV et al. | |
| 10,881,399 | B2 | 1/2021 | Shelton, IV et al. | |
| 11,462,324 | B1 | 10/2022 | Roh et al. | |
| 11,471,227 | B1 | 10/2022 | Roh et al. | |
| 11,589,888 | B2 | 2/2023 | Shelton, IV et al. | |
| 11,617,492 | B2 | 4/2023 | Refai et al. | |
| 12,144,561 | B2 | 11/2024 | Shelton, IV et al. | |
| 2014/0263552 | A1 | 9/2014 | Hall et al. | |
| 2015/0057675 | A1 | 2/2015 | Akeel et al. | |
| 2015/0209105 | A1 | 7/2015 | Margallo et al. | |
| 2017/0172594 | A1 | 6/2017 | Allen, IV | |
| 2017/0296213 | A1 | 10/2017 | Swensgard et al. | |
| 2017/0364831 | A1 | 12/2017 | Ghosh et al. | |
| 2018/0247128 | A1 | 8/2018 | Alvi et al. | |
| 2018/0289434 | A1 | 10/2018 | Palo et al. | |
| 2019/0125458 | A1 | 5/2019 | Shelton, IV et al. | |
| 2019/0125459 | A1 | 5/2019 | Shelton et al. | |
| 2019/0200844 | A1 | 7/2019 | Shelton, IV et al. | |
| 2019/0200981 | A1 | 7/2019 | Harris et al. | |
| 2019/0201046 | A1 | 7/2019 | Shelton, IV et al. | |
| 2019/0201047 | A1 | 7/2019 | Yates et al. | |
| 2019/0201137 | A1 | 7/2019 | Shelton, IV et al. | |
| 2019/0201140 | A1 | 7/2019 | Yates et al. | |
| 2019/0206003 | A1* | 7/2019 | Harris | G16H 20/40 |
| 2019/0206542 | A1 | 7/2019 | Shelton, IV et al. | |
| 2019/0206562 | A1 | 7/2019 | Shelton, IV et al. | |
| 2019/0206563 | A1 | 7/2019 | Shelton, IV et al. | |
| 2019/0206569 | A1 | 7/2019 | Shelton, IV et al. | |
| 2019/0231220 | A1 | 8/2019 | Refai et al. | |
| 2019/0279765 | A1 | 9/2019 | Giataganas et al. | |
| 2019/0325574 | A1 | 10/2019 | Jin et al. | |
| 2019/0362834 | A1 | 11/2019 | Venkataraman et al. | |
| 2020/0074692 | A1 | 3/2020 | Ooba | |
| 2020/0281670 | A1 | 9/2020 | Moskowitz et al. | |
| 2020/0375662 | A1 | 12/2020 | Lee et al. | |
| 2020/0405403 | A1 | 12/2020 | Shelton, IV et al. | |
| 2021/0076966 | A1* | 3/2021 | Grantcharov | G06N 20/00 |
| 2021/0205031 | A1 | 7/2021 | Shelton, IV et al. | |
| 2021/0275260 | A1* | 9/2021 | Kang | A61B 34/76 |
| 2021/0298795 | A1 | 9/2021 | Bowling et al. | |
| 2021/0322017 | A1 | 10/2021 | Shelton, IV et al. | |
| 2021/0370790 | A1 | 12/2021 | Feldman | |
| 2021/0393337 | A1 | 12/2021 | Zucker | |
| 2022/0108789 | A1 | 4/2022 | Shelton, IV et al. | |
| 2022/0233119 | A1 | 7/2022 | Shelton, IV et al. | |
| 2022/0354347 | A1 | 11/2022 | Nishimura et al. | |
| 2023/0028059 | A1 | 1/2023 | Shelton, IV et al. | |
| 2023/0079275 | A1 | 3/2023 | Wu et al. | |
| 2023/0098670 | A1 | 3/2023 | Shelton, IV et al. | |
| 2023/0101192 | A1 | 3/2023 | Shelton, IV et al. | |
| 2023/0101714 | A1 | 3/2023 | Shelton, IV et al. | |
| 2023/0101750 | A1 | 3/2023 | Shelton, IV et al. | |
| 2023/0101757 | A1 | 3/2023 | Hassan et al. | |
| 2023/0102358 | A1 | 3/2023 | Shelton, IV et al. | |
| 2023/0103005 | A1 | 3/2023 | Shelton, IV et al. | |
| 2023/0165649 | A1* | 6/2023 | Fitzsimons | A61B 34/30 700/245 |
| 2023/0181255 | A1* | 6/2023 | Roh | A61B 34/20 606/1 |
| 2023/0210612 | A1* | 7/2023 | Roh | A61B 34/25 700/102 |
| 2023/0338099 | A1* | 10/2023 | Roh | G16H 20/40 |
| 2023/0371950 | A1 | 11/2023 | Shelton, IV et al. | |
| 2023/0371968 | A1 | 11/2023 | Shelton, IV et al. | |
| 2023/0372012 | A1 | 11/2023 | Harris et al. | |
| 2023/0372013 | A1 | 11/2023 | Shelton, IV et al. | |
| 2023/0372030 | A1 | 11/2023 | Shelton, IV et al. | |
| 2023/0372031 | A1 | 11/2023 | Shelton, IV | |
| 2023/0377709 | A1 | 11/2023 | Shelton, IV et al. | |
| 2023/0377726 | A1 | 11/2023 | Shelton, IV et al. | |
| 2023/0397969 | A1 | 12/2023 | Shelton, IV et al. | |
| 2023/0404691 | A1 | 12/2023 | Shelton, IV et al. | |
| 2025/0278683 | A1 | 9/2025 | Nakayasu et al. | |

FOREIGN PATENT DOCUMENTS

| | | | |
|---|---|---|---|
| EP | 3506287 | A1 | 7/2019 |
| WO | 2018142277 | A1 | 8/2018 |
| WO | 2019117926 | A1 | 6/2019 |
| WO | 2021049438 | A1 | 3/2021 |

OTHER PUBLICATIONS

"IEEE Std 802.Nov. 2020 (Revision of IEEE Std 802.11-2016)", The Institute of Electrical and Electronics Engineers, Inc, Approved on Dec 3, 2020, 149 pages.

"The IEEE 802.3 Standard (Ethernet)", IEEE Computer Society, 2008, 634 pages.

Divakarla, Kavya Prabha, "ISO 26262 And IEC 61508 Functional Safety Overview", NXP: Secure Connections for Smarter World, Jun. 2017, 46 pages.

Yang et al., "A Dynamic Strategy for Packet Scheduling And Bandwidth Allocation Based on Channel Quality in IEEE 802.16e OFDMA System", Journal of Network and Computer Applications, vol. 39, Mar. 2014, pp. 52-60.

* cited by examiner

47245

DYNAMICALLY DETERMINING SURGICAL AUTONOMY LEVEL

CROSS-REFERENCE TO RELATED APPLICATIONS

This application is related to the following, filed contemporaneously, the contents of each of which are incorporated by reference herein:

U.S. patent application Ser. No. 17/747,806, entitled METHOD OF CONTROLLING AUTONOMOUS OPERATIONS IN A SURGICAL SYSTEM.

U.S. patent application Ser. No. 17/747,714, entitled DETECTING FAILURE MITIGATION ASSOCIATED WITH AUTONOMOUS SURGICAL TASK.

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices.

SUMMARY

A surgical task may be automated. A device may receive an indication of a surgical task to be performed with a surgical instrument. Capabilities of the surgical instrument may be associated with levels of automation. The device may monitor a performance of the surgical task with the surgical instrument operating at a first level of automation associated with the levels of automation. The device may detect a trigger event associated with the performance of the surgical task and switch operation of the surgical instrument from the first level of automation to a second level of automation associated with levels of automation, for example, based on the trigger event. The capabilities of the surgical instrument may include a set of surgical instrument tasks and the level of automation may be associated with automating one or more surgical instrument tasks from the set of surgical instrument tasks. The performance of the surgical task may be based on real-time surgical data. The real-bane surgical data may include one or more of the following: user data, surgical environment data, surgical instrument data, task data, historical data, or the like. In example, the device may detect the trigger event by comparing the performance of the surgical task with a trigger event threshold and may switch operation of the surgical instrument from the first level of automation to the second level of automation based on the trigger event. The second level or automation may be associated with automating less surgical instrument tasks when compared to the first level of automation. Monitoring the performance of the surgical task may include comparing one or more of the real-time surgical data to respective ideal surgical data.

In examples, the device may operate at a first level of automation of the levels of automation associated with the surgical task. The device may obtain an indication to switch to a second level of automation of the levels of automation associated with the surgical task. The indication may be based on detecting a trigger. The device may operate at the second level of automation of the levels of automation associated with the surgical task based on the indication. The indication may be based on monitoring a performance of the first level of automation. The performance of the first level of automation may be based on real-time surgical data.

DETAILED DESCRIPTION

Figure 1:
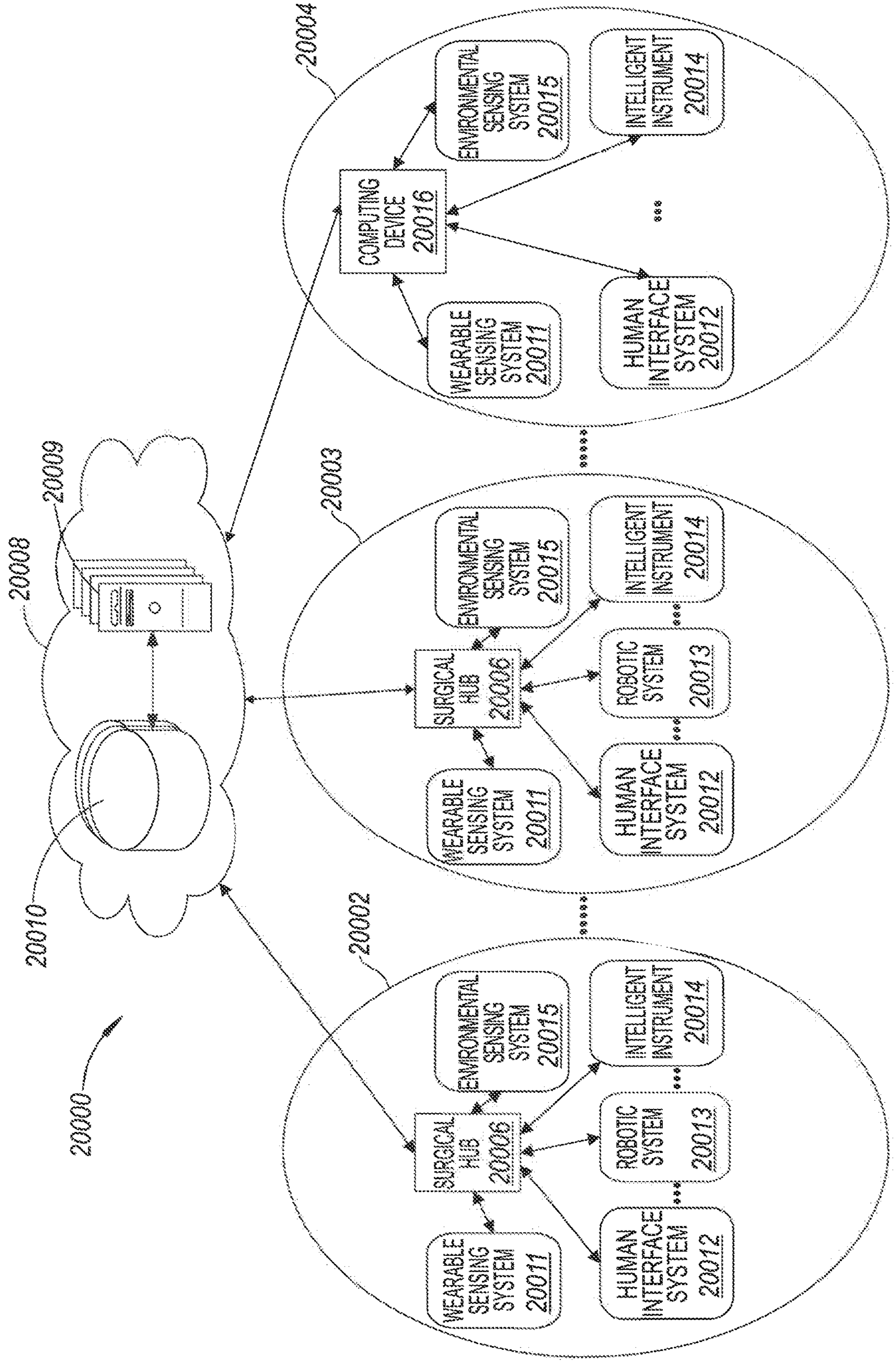
FIG. 1 is a block diagram of a computer-implemented surgical system.

FIG. 1 is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG, 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as farther described in FIG. 2.

The surgical system 20002 may be in communication with a remote server 20009 that may be part of a cloud computing system 20008. In an example, the surgical system 20002, may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems') and the environmental sensing system 20015 as discussed in FIG. 1. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which herein incorporated by reference in its entirety.

Figure 2:
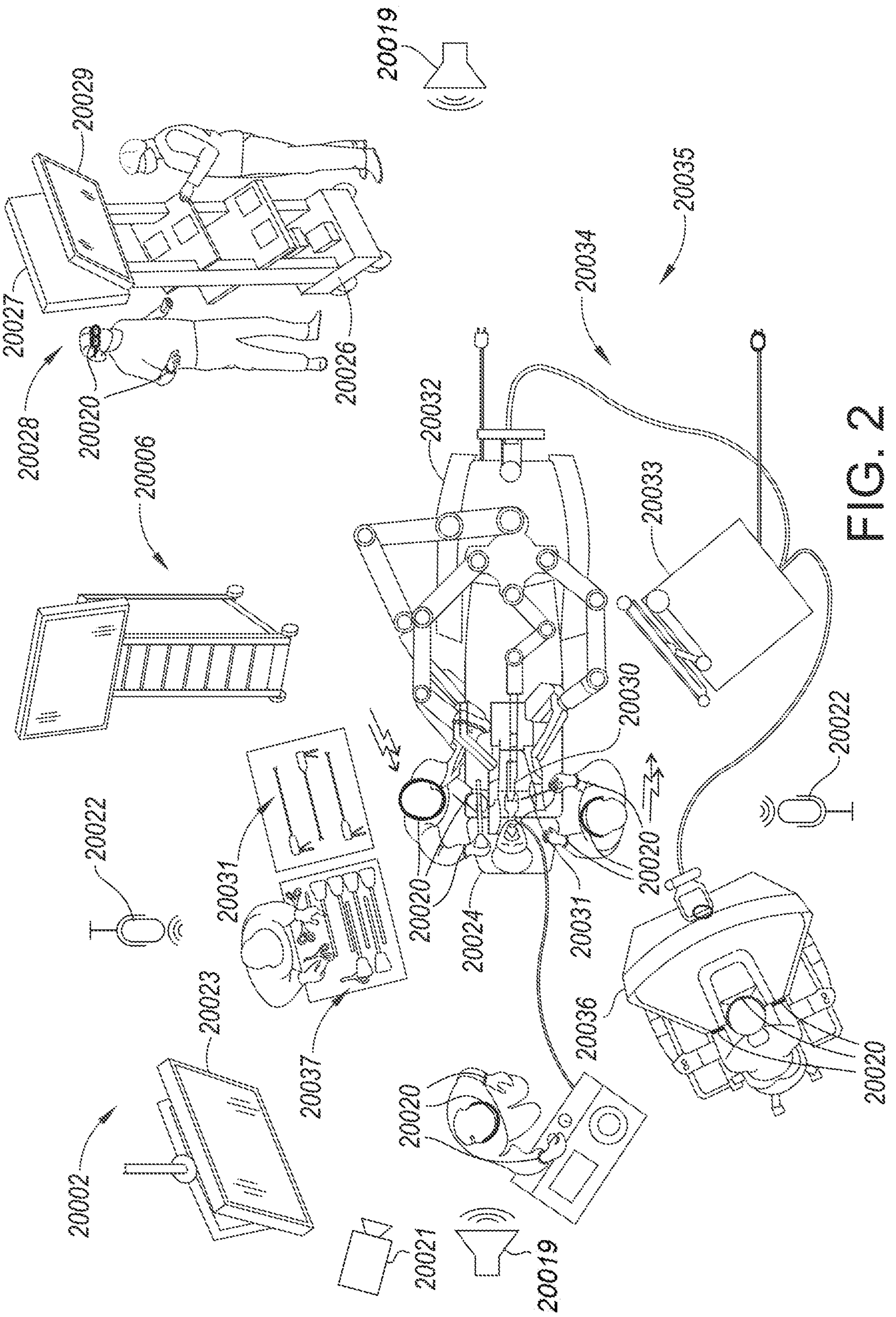
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/ humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging, device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater titan about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area, Wearable sensing system 20011 illustrated in FIG. 1 may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surrounding in the surgical theater, etc. The surgical hub 20006, alone or in communication with the cloud computing system, may use the surgeon biomarker measurement data and/or environmental sensing information to modify the control algorithms of hand-held installments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with HCP to adaptively control one or inure surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
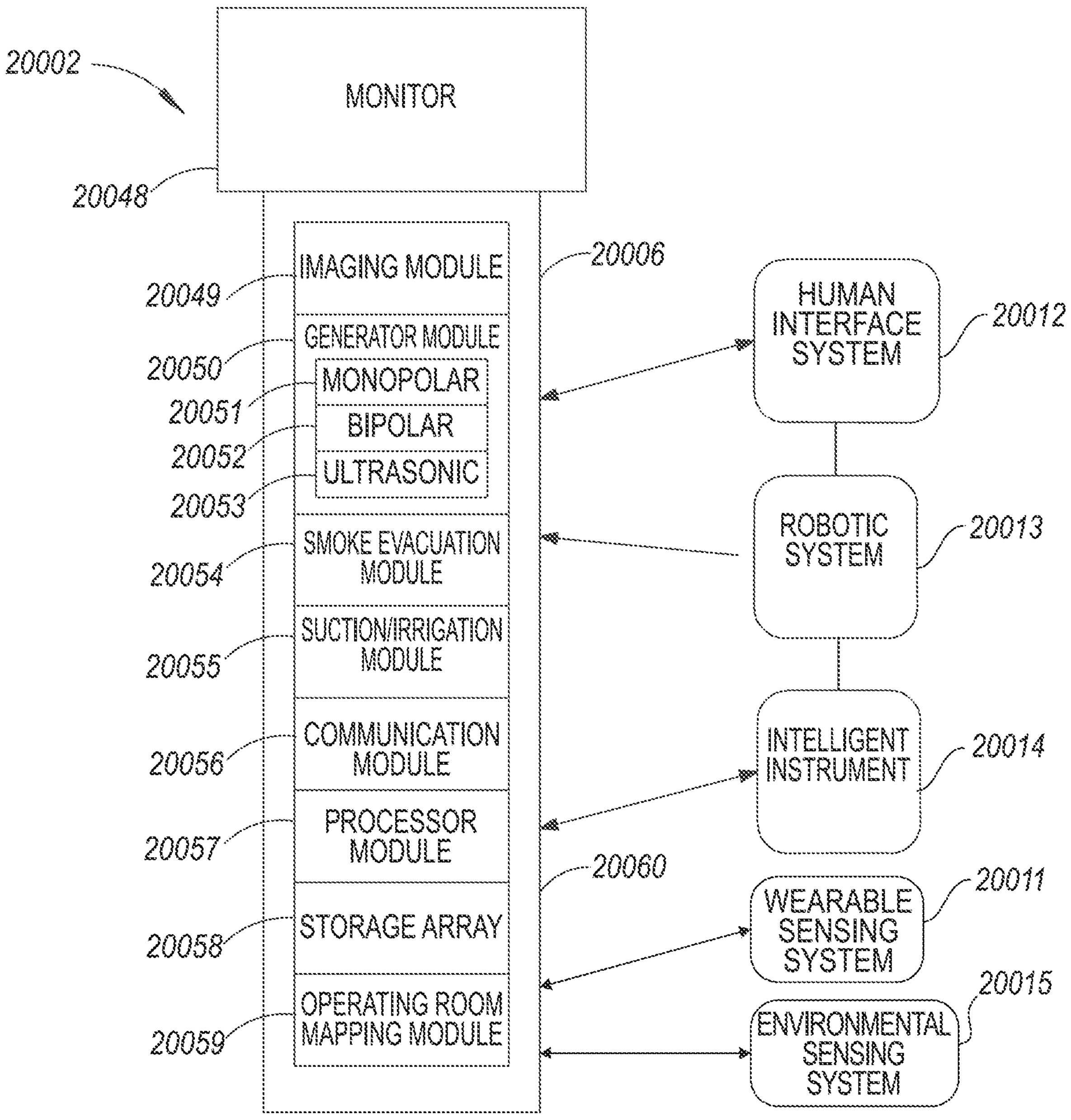
FIG. 3 illustrates an example surgical hub paired various systems.

FIG. 3 shows an example surgical system 20002 with a surgical hub 20006. The surgical hub 20006 may be paired with, via a modular control, a wearable sensing system 20011, an environmental sensing system 20015, a human interface system 20012, a robotic system 20013, and an intelligent is 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. The various modules and systems may be connected to the modular control either directly via a router or via the communication module 20056. The operating theater devices may be coupled to cloud computing resources and data storage via the modular control. The human interface system 20012 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and; or replacement of various modules. Aspects of the present disclosure present a modular surgical enclosure for use in a surgical procedure that involves energy application to tissue. The modular surgical enclosure includes a first energy-generator module, configured to generate a First energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The huh modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and; ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
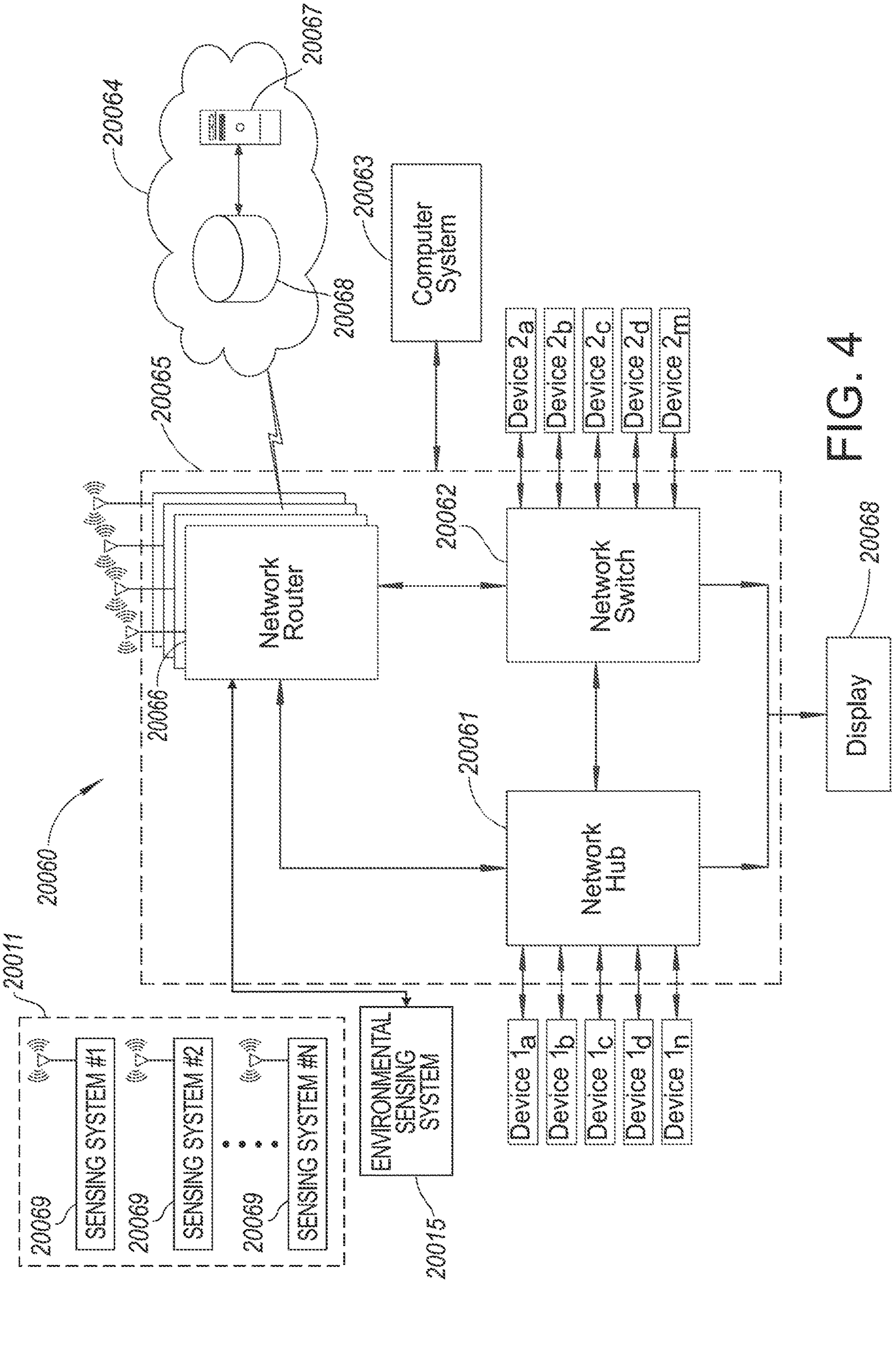
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs con figured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in. FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 200(35 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (RUM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety- features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A User may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USE. The output device(s) use sonic of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 2006.3 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring; IEEE 802.5, and the like. WAN technologies may include, but are not limited to, point-to-point links, circuit-switching networks like integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 20065. The network hub 20061 and/or the network switch 20062 may coupled to a network router 20066 to connect the devices 1*a*-1*n* to the cloud computing system 20064 or the local computer system 20063. Data associated with the devices 1*a*-1*n* may be transferred to cloud-based computers via the router for remote data processing and manipulation. Data associated with the devices 1*a*-1*n* may also be transferred to the local computer system 20063 for local data processing and manipulation. Modular devices 2*a*-2*m* located in the same operating theater also may be coupled to a network switch 20062. The network switch 20062 may be coupled to the network hub 20061 and/or the network router 20066 to connect the devices 2*a*-2*m* to the cloud 20064. Data associated with the devices 2*a*-2*m* may be transferred to the cloud computing system 20064 via the network router 20066 for data processing and manipulation. Data associated with the devices 2*a*-2*m* may also be transferred to the local computer system 20063 for local data processing and Manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1*a*-1*n*/2*a*-*m*. The local computer system 20063 also may be contained in a modular control tower. The modular communication hub 20065 may be connected to a display 20068 to display images obtained by some of the devices 1*a*-1*n*/2*a*-2*m*, for example during surgical procedures. In various aspects, the devices 1*a*-1*n*/2*a*-2*m* may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1*a*-1*n*/2*a*-2*m* of the sensing systems 20069 to the cloud-base system 20064. One or more of the devices 1*a*-1*n*/2*a*-2*m* or the sensing systems 20069 coupled to the network hub 20061 or network switch 20062 may collect data in real-time and transfer the data to cloud computers for data processing, and manipulation. It will be appreciated that cloud computing relies on sharing computing resources rather than having local servers or personal devices to handle software applications. The word "cloud" may be used as a metaphor for "the Internet," although the term is not limited as sects. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud--based computing to examine data including images of samples of body tissue for diagnostic purposes. This may include localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud computing system 20064 or the local computer system 20063 or both for data processing and manipulation including image processing and manipulation. The data may be analyzed to improve surgical procedure outcomes by determining if farther treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 2006 the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1*a*-1*n* may be connected to the modular communication hub 20065 over a wired channel or a wireless channel depending on the configuration of the devices 1*a*-1*n* to a network hub 20061. The network hub 20061 may be implemented, in one aspect, as a local network broadcast device that works on the physical layer of tile Open System Interconnection (OSI) model. The network hub may provide connectivity to the devices 1*a*-1*n* located in the same operating theater network. The network hub 20061 may-collect data in the form of packets and sends them to the router in half duple mode. The network hub 200611 may not store any media access control/Internet Protocol (MAC/IP) to transfer the device data. Only one of the devices 1*a*-1*n* can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2*a*-2*m* may be connected to a network switch 20062 over a wired channel or a wireless channel. The network switch 20062 works in the data link layer of the OSI model. The network switch 20062 may be a multicast device for connecting the devices 2*a*-2*m* located in the same operating theater to the network. The network switch 20062 may send data in the form of frames to the network router 20066 and may work in full duplex mode. Multiple devices 2*a*-2*m* can send data at the same time through the network switch 20062. The network switch 20062 stores and uses MAC addresses of the devices 2*a*-2*m* to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for farther processing and manipulation of the data collected by any one of or all the devices 1*a*-1*n*/2*a*-2*m* and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In examples, the operating theater devices 1*a*-1*n*/2*a*-2*m* and/or the sensing systems 20069 may communicate to the modular communication hub 20065 via. Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1*a*-1*n*/2*a*-2*m* and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1*a*-1*n*/2*a*-2*m* and the sensing systems 20069 and may handle a data type known as frames. Frames may carry the data generated by the devices 1*a*-1*n*/2*a*-2*m* and/or the sensing systems 20069. When a frame is received by the modular communication hub 20065, it may be amplified and sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1*a*-1*n*/2*a*-2*m*.

Figure 5:
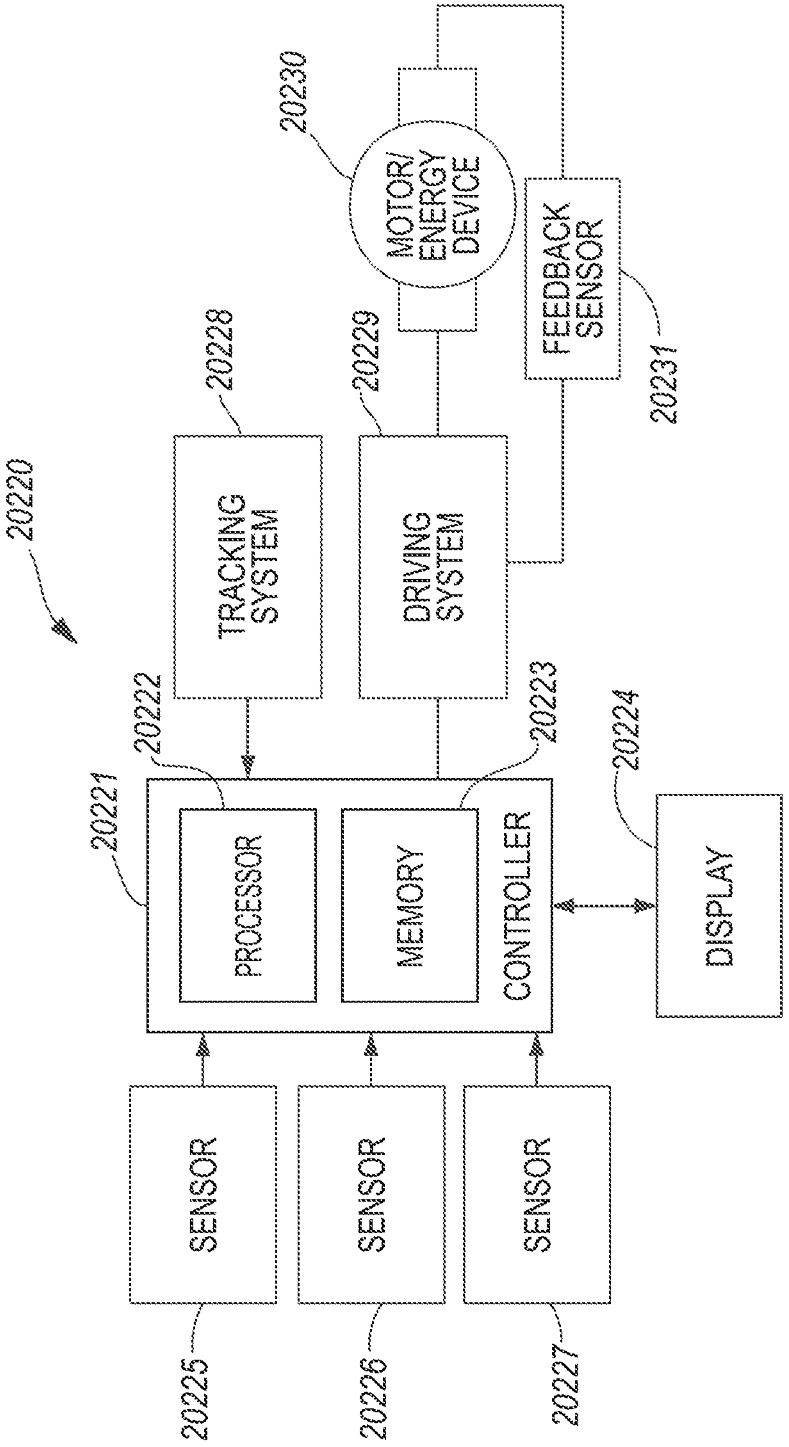
FIG. 5 illustrates a logic diagram of a control system of a surgical instrument.

FIG. 5 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which cart be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PW modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3911 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam, Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetosinctive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (COMIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 composing an absolute positioning: system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensors) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 20117, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 2022,7, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the surgical hub 20065 as shown in FIG. 4.

Figure 6:
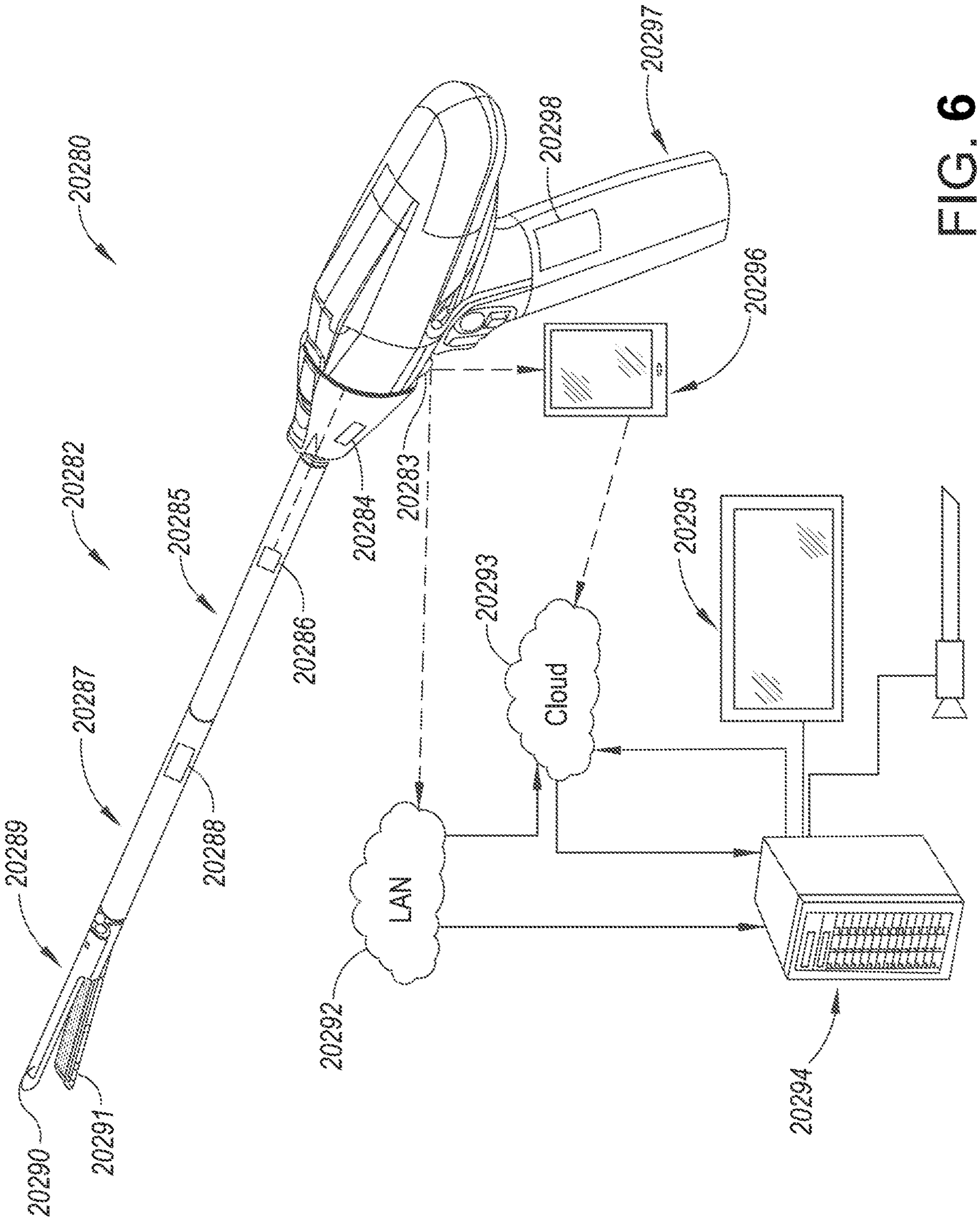
FIG. 6 shows an example surgical system that includes a handle having a controller and a motor, an adapter releasably coupled to the handle, and a loading unit releasably coupled to the adapter.

FIG. 6 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touch screens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of, the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit is data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter it from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 7:
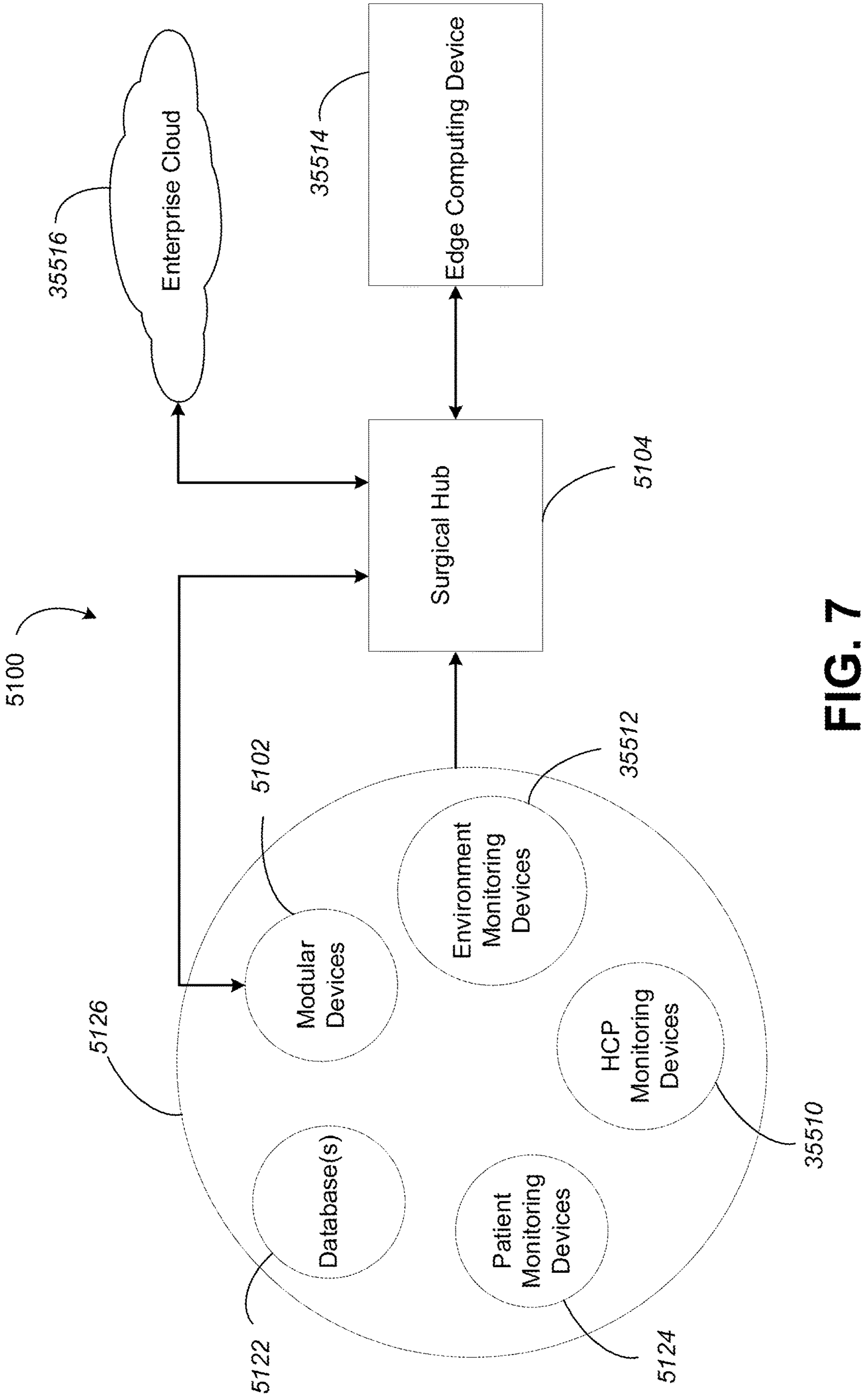
FIG. 7 shows an example situationally aware surgical system.

FIG. 7 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring, devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual in formation regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual is formation received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular-data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Surgical autonomous systems, devices, and methods may include aspects of integration with other medical equipment, data sources, processes, and institutions. Surgical autonomous systems, devices, and methods may include aspects of integration with a computer-implemented interactive surgical system and/or with one or more elements of a computer-implemented interactive surgical system, for example. Surgical system, surgical autonomous system, and autonomous surgical system may be interchangeably as described herein.

Figure 8:
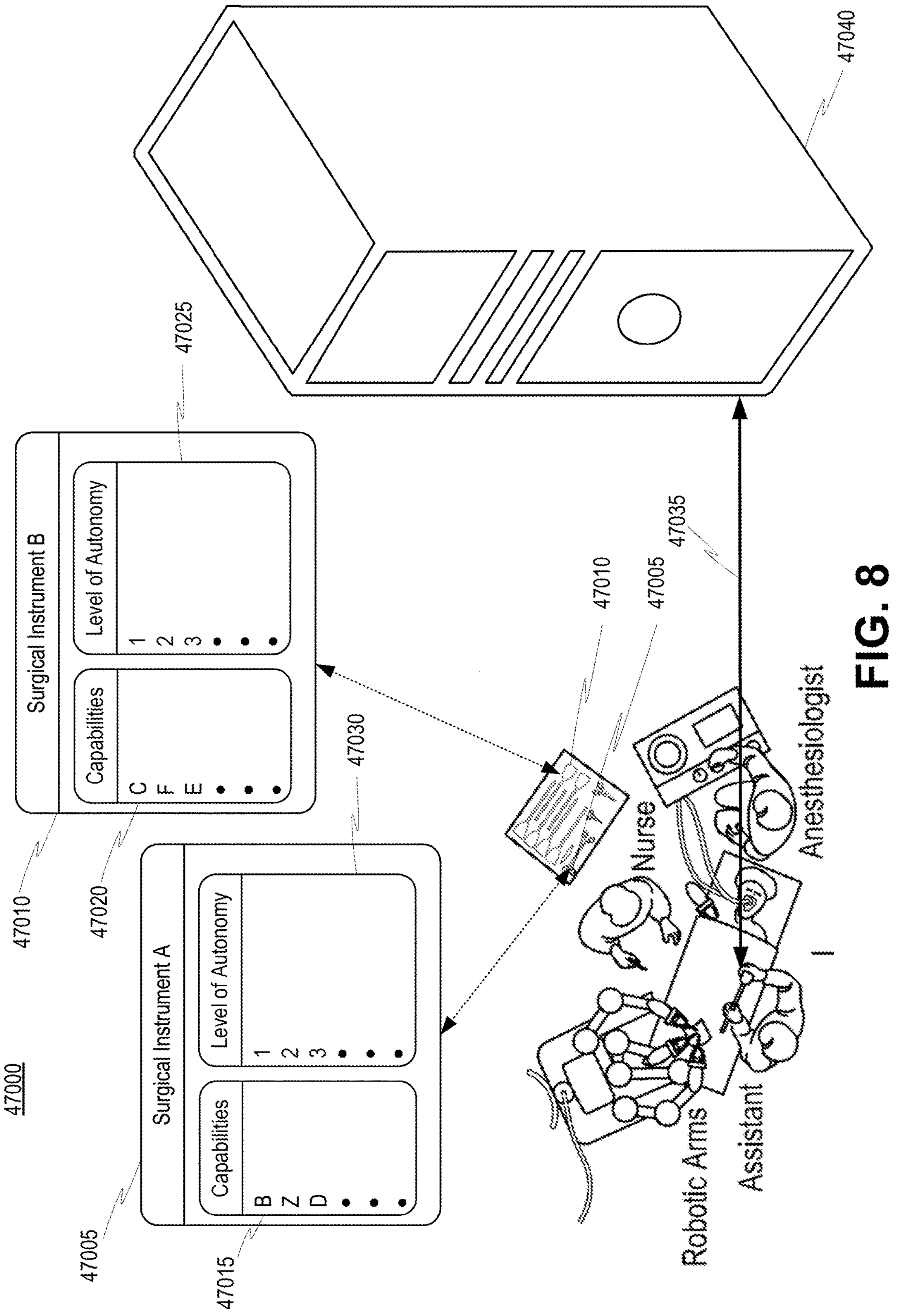
FIG. 8 shows an example of a surgical autonomous system.

Referring to FIG. 8, an overview of the surgical autonomous system 47000 may be provided. Surgical instrument A 47005 and/or surgical instrument B 47010 may be used in a surgical procedure as part of the surgical system 47000. The surgical hub 47040 may be configured to coordinate information flow to a display of the surgical instrument. For example, the surgical hub may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4. 2018, the disclosure of which is herein incorporated by reference in its entirety. Example surgical instruments that are suitable for use with the surgical system 47000 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 8 shows an example of a surgical autonomous system 47000. The system 47000 may be used to perform a surgical procedure on a patient who is lying down on an operating table in a surgical operating room. A robotic system may be used in the surgical procedure as a part of the surgical system. For example, the robotic system may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. The robotic hub may be used to process the images of the surgical site for subsequent display to the surgeon through the surgeon's console.

Other types of robotic systems may be readily adapted for use with the surgical system 47000. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, an imaging device may be used in the surgical system 47000 and may include at least one image sensor and one of more optical components. Suitable image sensors may include, but are not limited to, Charge-Coupled Device (CCD) sensors and Complementary Metal-Oxide Semiconductor (CMOS) sensors.

The optical components of the imaging device may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may be referred to as visible light or simply light. A typical human eye will respond to wavelengths in air that are from about 380 nm to about 750 nm.

The invisible spectrum (e.g., the non-luminous spectrum is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device may be configured for use in a minimally invasive procedure. Examples of imaging devices suitable Or use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment mom, necessitate the highest possible sterility of all medical devices and equipment. Part of that sterilization process is the need to sterilize anything that comes in contact with the patient or penetrates the sterile field, including the imaging device and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

As described with respect to FIGS. 2, 3, 5, and 7, surgical instrument A 47005 and/or surgical instrument B 47010 may comprise one or more capabilities (e.g., capabilities 47015 associated with surgical instrument A 47005 which may comprise B, Z, and D and capabilities 47020 associated with surgical instrument B 470010 which may comprise C, F, and E). The capabilities may be associated with features that the surgical instrument is capable of performing. Examples of the features may be described under the heading "Surgical instrument Hardware" and in U.S. Patent Application Publication No. US 2019-0200844 A1 (U.S. patent application Ser. No. 16/209,385), titled METHOD OF HUB COMMUNICATION, PROCESSING-, STORAGE AND DISPLAY, filed Dec. 4, 2018, the disclosure of which is herein incorporated by reference in its entirety, for example. For example, if the surgical instrument is an endocutter, one of the capabilities may be resecting tissue (e.g., tissue surrounding a colon when the surgeon in performing a colorectomy). The capabilities may comprise surgical tasks as described with respect to FIG. 9. For example, the capability of resecting tissue may comprise controlling an energy source; cutting, stapling, knob orientation, body orientation, body position, anvil jaw force, reload alignment slot management, and/or the like.

The capabilities (e.g., each of the capabilities) of surgical instrument A 47005 and/or surgical instrument B 47010 may be associated with respective autonomy levels (e.g., capabilities 47015 associated with surgical instrument A 47005 may be associated with levels of autonomy 47030 and capabilities 47020 associated with surgical instrument B 470010 may be associated with autonomy levels 47025). For example, the autonomy levels may be categorized by numbers such as 1, 2, 3, etc. 1 may represent an autonomy level with the least manual input when compared to the other autonomy levels. For example, an autonomy level with the least manual input may result in the user of the surgical instrument having to perform less surgical tasks associated with the capability when compared to other levels of autonomy. If the surgical instrument is an endocutter and the capability is resecting tissue, autonomy level 1 may result in the surgeon having only to perform controlling the energy source whereas autonomy level 2 may result in the surgeon having to perform controlling an energy source, body orientation, and/or body position. The tasks not performed by the surgeon may be performed using an autonomous function.

Figure 10:
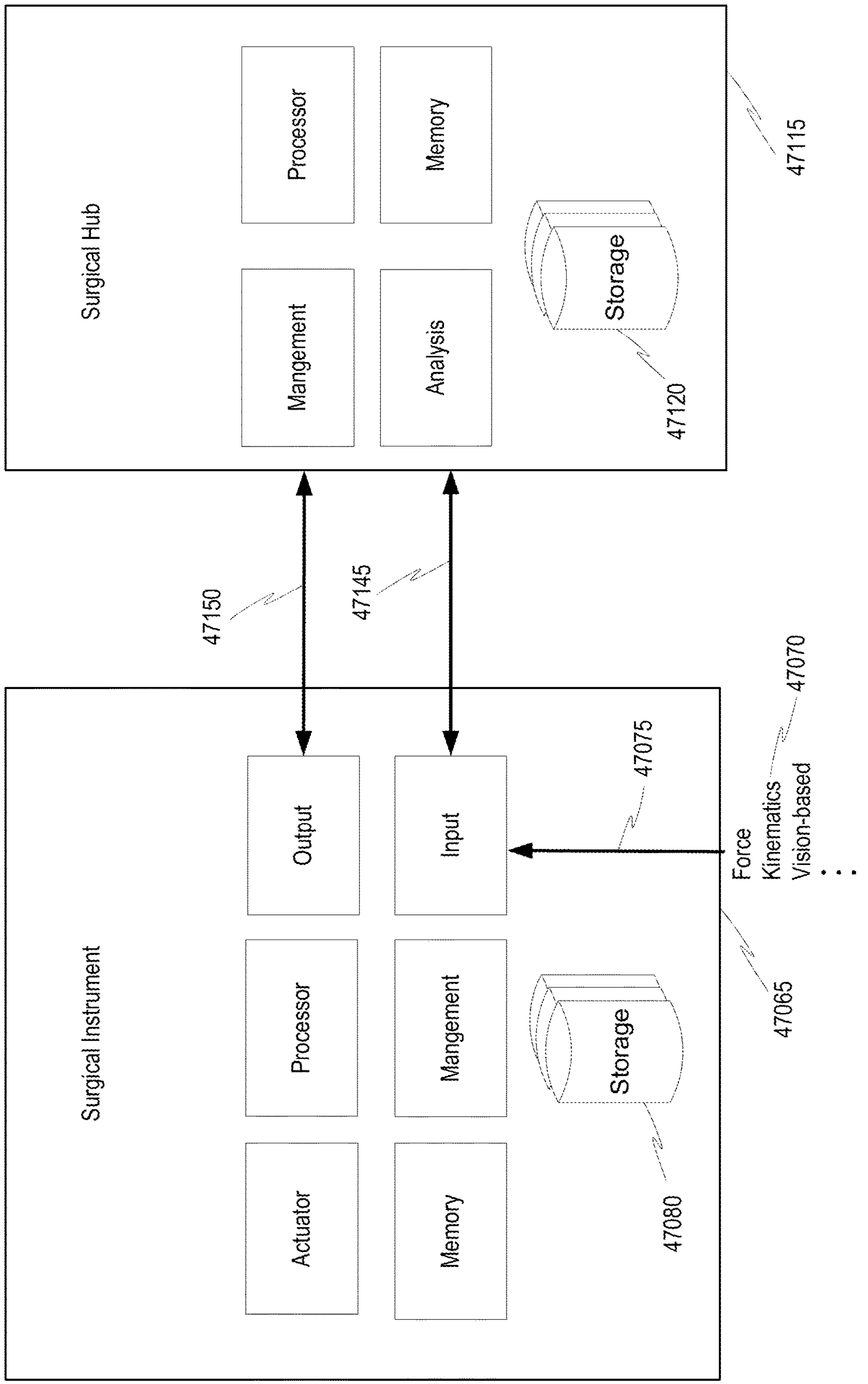
FIG. 10 shows an example of computer-implemented autonomous surgical system.
Figure 11:
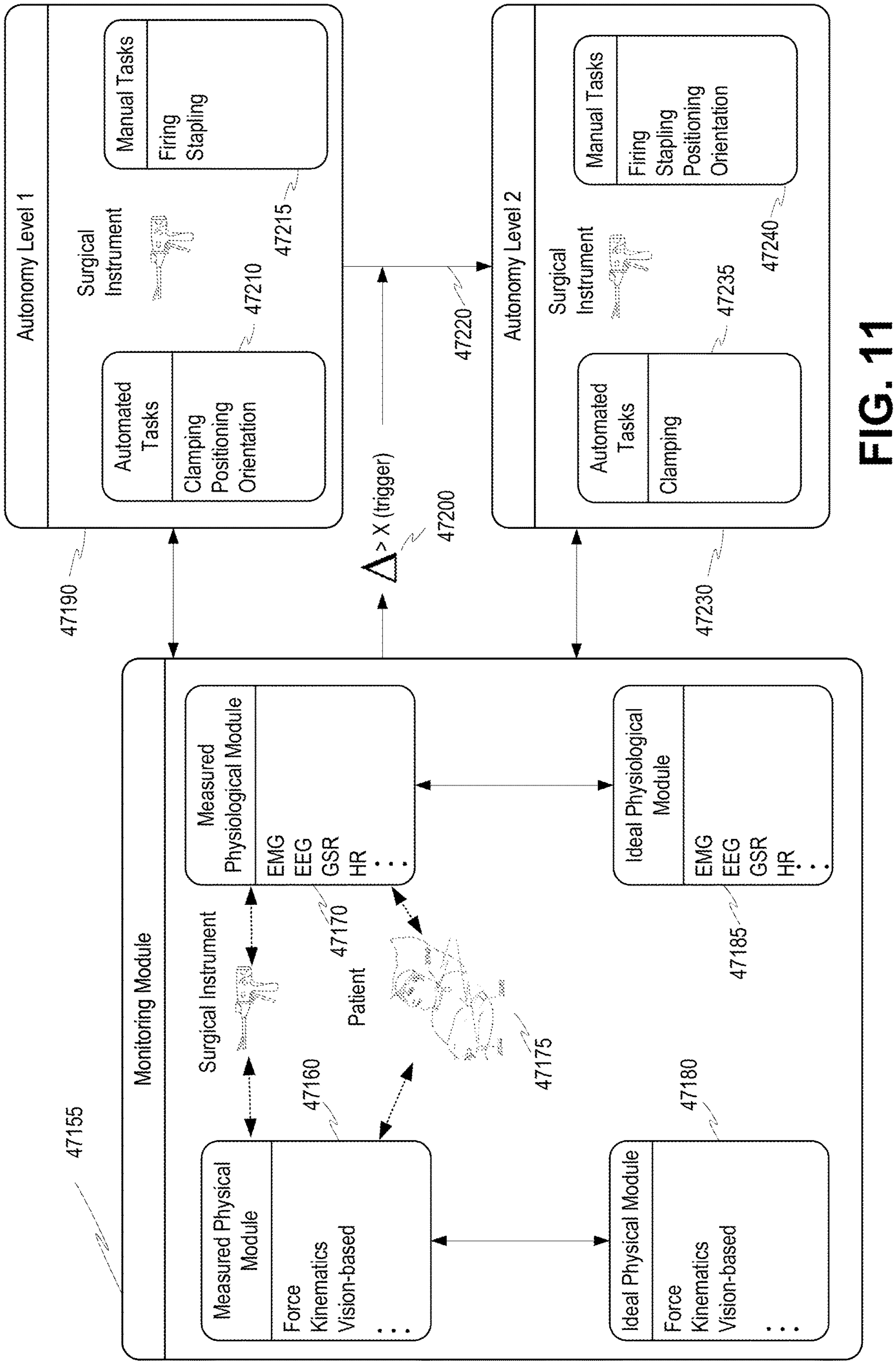
FIG. 11 shows an example of monitoring the performance of surgical tasks associated with autonomy levels.

Data may be generated (e.g., by a monitoring module located at the surgical hub 47040 or locally by the surgical instrument as described with respect to FIG. 11) based on the performance of surgical instrument A 47005 and/or B 47010. The data may be relevant to how the current level of autonomy at which the surgical instrument is operating is doing in terms of performance. For example, the data may be associated with physical measurement physiological measurements, and/or the like as described with respect to FIGS. 10 and 11. The measurements are described in greater detail under the heading "Monitoring of Adjusting A Surgical Parameter Based. On Biomarker Measurements" in U.S. patent application Ser. No. 17/156,28, filed Nov. 10, 2021, the disclosure of which is herein incorporated by reference in its entirety.

Ar indication 47035 of the data may be transmitted to the surgical hub 47040, for example, where it may be evaluated. In examples, the indication 47035 may be transmitted to a cloud service (e.g., amazon web services) as described herein. The data may be used as input in an analysis module, for example, to check if the performance of the surgical instrument falls within a satisfactory range. The surgical instrument may comprise a capability associated with a current level of autonomy (e.g., autonomy level If the data related to the performance falls outside the range (e.g., crosses a threshold as described with respect to FIGS. 11 and 9), the surgical hub 47040 may send an indication 47035 back to the surgical instrument (e.g., surgical instrument A 47005 and/or B 47010) to switch the level of autonomy associated with the capability. For example, resecting tissue may be switched from autonomy level 1 to autonomy level 2 if data related to performance crosses a threshold.

Figure 9:
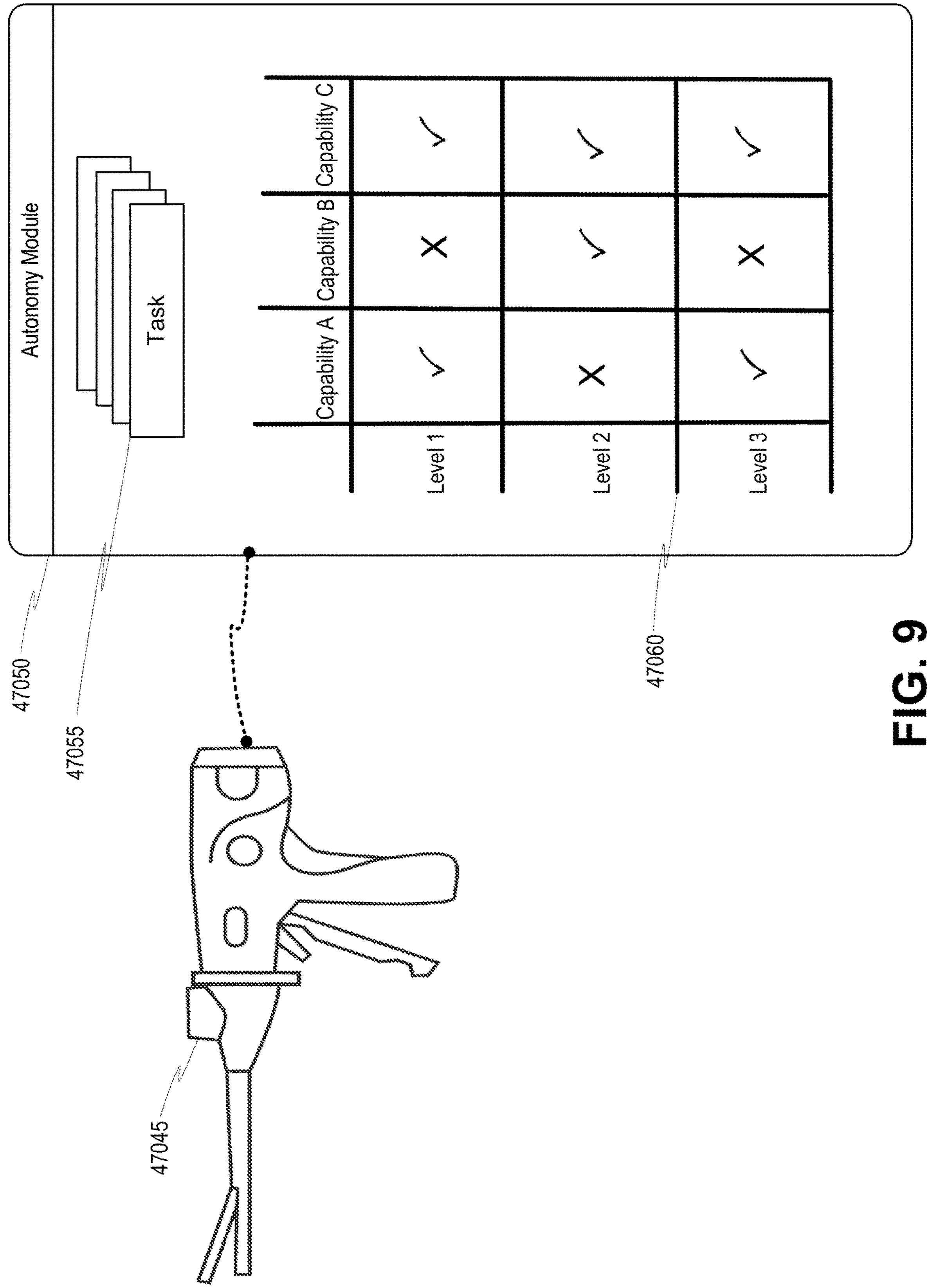
FIG. 9 shows an example of an autonomy module associated with a surgical instrument and surgical instrument capabilities.

FIG. 9 shows an example of an autonomy module 47050 associated with a surgical instrument 47045 and surgical instrument capabilities 47060. The autonomy module 47050 may be associated with a surgical instrument 47045. In examples, the autonomy module 47045 may be part of the surgical instrument's software. In examples, the autonomy module 47045 may be part of the surgical hub as described with respect to FIG. 8. The autonomy module 47045 may keep track of the link between the surgical instrument's capabilities 47060 and the level of autonomy. For example, the autonomy module 47050 may reference, e.g., via a query, a database (e.g., structured query language (SQL) database) that maintains the link between capabilities 47060 and autonomy levels at a given time (e.g., maintains that, at the current time, capability A is running on autonomy level 1). The database may be updated based on the autonomy level associated with a capability changing. In examples, the database may link the one or more tasks 47055 to the autonomy level. In such a case, the capability 47060, autonomy level associated with the capability 47060, and the surgical tasks 47055 associated with the autonomy level may be linked and queried by the autonomy module.

In examples, the autonomy module 47050 may comprise all surgical tasks associated with the surgical instrument 47045. The autonomy module 47050 may append the surgical tasks into data structures (e.g., lists) that are associated with respective capabilities 47060. The module 47050 may designate one or more surgical tasks 47055 for the surgical instrument 47045 to perform autonomously based on the capability 47060 and the autonomy level as described herein. For example, the surgical instrument 47045 may be an endocutter. The endocutter's capability may be resecting a tissue and the autonomy level for this capability 47060 may be 1. The autonomy module 47050 may designate controlling the energy source, cutting, stapling, knob orientation, body orientation, body position, anvil jaw force, and reload alignment slot management to be performed autonomously. In such a case, if the capability 47060 switched to autonomy level 2, the autonomy module 47050 may designate less tasks 47055 to be performed autonomously. For example, for autonomy level 2, the autonomy module 47055 may designate body position, anvil jaw force, and reload alignment slot management to be performed autonomously. The other tasks 47055 may be performed manually by a surgeon.

A surgical instrument 47045 may comprise capabilities 47060 where each capability 47060 can only operate at certain autonomy levels. In examples, the autonomy module 47050 may reference a rules engine to check if the capability 47060 is permitted to operate at a given autonomy level. For example, capability A may be organ mobilization. Tissue mobilization may only allow the surgical instrument 47045 to operate at autonomy level 1 or autonomy level 3 (e.g., as shown in FIG. 9). Capability B may be anastomosis. Anastomosis may only allow the surgical instrument 47045 to operate at autonomy level 2 (e.g., as shown in FIG. 9.

FIG. 10 shows an example of computer-implemented autonomous surgical system. The system may comprise a processor associated with the surgical instrument 47065 and a processor associated with the surgical hub 47115. The surgical instrument processor may be coupled to a communication (e.g., communication module), storage 47080, memory (e.g., non-volatile memory), management module, actuator(s), and sensors), input interface (e.g., which may obtain 47075 measurements 47070 such as physical, physiological, and vision-based as described with respect to FIGS. 9 and 11, from an external source), and output interface via a system bus. The system bus may be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The surgical hub processor may be coupled to communication, storage 47080, memory (e.g., non-volatile memory), input/output interfaces, analysis module, and management module via a system bus.

Each processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 a prefetch buffer to improve performance above 40 MHz, a 32 KB single-cycle serial random access memory (SRAM.), an internal read--only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In examples, each processor may comprise a safety controller comprising two controller-based families such as TMS570 and RM4x, known under the trade name Hercules ARM Cortex R4 also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SRAM), enhanced SDRAM (ESDRAM), Synchlink DRAM (SL-DRAM), and direct Rambus RAM (DRRAM).

The system may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the system may include software that acts as an intermediary between users and the basic computer resources described in a suitable operating environment. Such software may include an operating system. In examples, the operating system may be associated with the management modules for the surgical instrument 47065 and surgical hub 47115, respectively. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the system through input device(s) coupled to the I/O interface. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. The output device may be the surgical hub 47115. The output device may be the surgical instrument 47065. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The system may operate in a networked environment using logical connections to one or more remote computers, such as cloud computer(s) (e.g., as described with respect to FIG. 8), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system. The hardware/software necessary for connection to the network interface may include, for illustrative purposes only, internal and external technologies such as modems, including regular telephone-grade modems, cable modems, and DSL modems, ISDN adapters, and Ethernet cards.

The surgical instrument 47065 may include one or more hardware components such as actuators, sensors, etc. As the surgical instrument is performing a surgical, data may be generated from the hardware components, communicated to the surgical instalment's memory, and archived in the surgical instrument's storage 47080. The data may relate to physical, physiological, vision-based, etc. conditions of the surgical instrument's performance. As described herein, data may be received 47075 by the surgical instrument: from an outside source. Physical. conditions may relate to the force that the surgical instrument is applying (e.g., such as a mechanical grasp) and/or the kinematics of the surgical instrument 47065 (e.g., position, speed, and/or orientation of the instrument).

The data (e.g., an indication 47150 of the data) may be transmitted via the communication, as described herein, to the surgical hub 471115. The surgical hub 47115 may use the data as input in an analysis module. The analysis module may assess whether the data crosses the threshold (e.g., is within the range of satisfactory outcome as described with respect to FIGS. 9 and 11). In examples, the analysis module may be a cloud service, such as Amazon Web Services's (TM) (AWS)'s lambda function. The surgical hub 47115 may archive the data in storage 47120 (e.g., data may be used for a subsequent surgery). The data may be analyzed (e.g., by the analysis module) and an indication 47145 of the analyzed data may be sent back to the surgical instrument 47065 as input.

FIG. 11 shows an example of monitoring the performance of surgical tasks associated with autonomy levels. A monitoring module 47155 may be part of the surgical instrument, surgical hub, or a remote device (e.g., a third-party cloud service). In examples, aspects of the monitoring module 48155 may be distributed among multiple devices (e.g., each device may be responsible for executing a certain set of instructions). The monitoring module 47155 may be the analysis module as described with respect to FIG. 10. The monitoring module 47155 may assess whether the performance of the surgical instrument capability, operating at an autonomy level, is within an acceptable (e.g., satisfactory) range.

The monitoring module 48155 may obtain data associated with the surgical instrument and/or patient 47175, as is shown in FIG. 11. The data may be generated from an external source (e.g., a wearable on the patient 47175 that measures biomarker data) and an indication of the data may be transmitted to the monitoring module 47155 a message. The message may be in response to the monitoring module 47155 requesting the data via a request message. The data may be in raw form and may be transformed by the processor (e.g., the surgical hub processor or the surgical instrument processor as describe; respect to FIG. 10) into a form suitable for analysis.

The data may relate to the performance of the surgery. For example, the data may relate to measured physiological conditions of the patient 47175, surgeon, and/or staff who are participating in the surgery. For example, die patient 47175 may be wearing a heart rate monitoring wearable. Monitoring wearables are described in greater detail under the heading "Method Of Adjusting A Surgical Parameter Based On Biomarker Measurements" in U.S. patent application Ser. No. 17/156, 28, filed Nov. 10, 2021, the disclosure of which is herein incorporated by reference in its entirety. In such a case, data related to the patient's heart rate may be obtained and used by the monitoring module. The surgeon may be wearing a headband wearable that measures stress via sweat sensors (e.g., by deducing the level of cortisol that the surgeon is producing). The data related to the measured physiological conditions may be organized in a measured physiological module 47170, which may be a part of the monitoring module 47155.

The data may relate to measured physical conditions of the instrument, patient 47175, surgeon, and/or staff. For example, potentiometers and/or sensors may be placed on the surgical instrument and data related to the instrument's movement and/or orientation may be generated and sent to the monitoring module 47155. For example, the instrument, performing tasks autonomously based on its autonomy level as described with respect to FIG. 9, may move from position A to position B. The rate at which the instrument moved may be calculated (e.g., based on calculating readings from the potentiometers) and an indication of the rate may be transmitted to the monitoring module. In examples, the measured physical conditions may be obtained via data produced by a vision-based device. This data may be organized in the measured physical module 47160. In an example, physical and/or physiological conditions may be objects of operation. In an example, conditions other than physical and/or physiological may be objects of operation.

The monitoring module 47155 may be in communication with a surgical instrument. The surgical instrument may comprise a capability and the surgical instrument may be operating at a current autonomy level, for example, autonomy level 1 47190 as shown in FIG. 11, to perform the capability. Operating at autonomy level 1 47190 may result in the surgical instrument performing a number of tasks associated with the capability autonomously. For example, the automated tasks 47210 may be clamping, positioning, and orientation as shown in FIG. 11. This may leave the other tasks associated with the capabilities of firing and stapling to be performed manually (e.g., by the surgeon). Data related to the automated tasks 47210 and manual tasks 47215 may be generated and transmitted to the monitoring module 47155. The data may be organized in the measured physical module 47160 as described herein.

The monitoring module 47155 may include an ideal physical module 47180 and/or an ideal physiological module 47185. The module(s) may include the ideal values associated with a number of physical and physiological conditions. The ideal value may be dynamic and change based on the surgical context. For example, the ideal value associated with a surgeon's heart rate may increase if the surgeon is at a critical stage of the surgery. The ideal values may be generated based on historical data as described with respect to FIG. 9. The ideal values may be entered manually, for example, by the surgeon or other healthcare expert. In examples, the measured physical module 47160, measured physiological module 47170, ideal physical module 47180, and ideal physiological module 47185 may be organized in a different format.

The monitoring module 47155 may compare the measured physical module 47160 and measured physiological module 47170 to the ideal physical module 47180 and ideal physiological module 47185, respectively. In examples, an analysis module may be included in the monitoring module 47155 and may be responsible for assessing the comparison. The difference between the measured modules and ideal modules may be calculated and a delta output 47200 may be generated. In examples, each physiological condition may be assigned a weight and the weights may be considered when generating the delta output 47200. In examples, only a subset of the measured physical and/or measured physiological conditions may be compared to the ideal conditions, which may be determined based on surgical context as described with respect to FIG. 9.

The delta output 47200 may be compared to a trigger (e.g., trigger event), for example, to assess whether the trigger has been met. This trigger-may represent whether the difference between the measured modules and ideal modules exceeds an acceptable value and/or range. In examples, a delta output 47200 may be generated for each physiological and/or physical conditions and each delta output 47200 may be compared to respective triggers.

Based on the trigger being met, the autonomy level associated with the surgical instrument capability may switch 47220 to another autonomy level. In examples, the autonomy level may only switch to autonomy levels that are allowed for the capability as described with respect to FIG. 9. As shown in FIG. 11, the trigger has been Met and the autonomy level that the surgical instrument is operating at to perform its capability switched 47220 from autonomy level 1 47190 to autonomy level 2 47230. Autonomy level 2 47230 may result in less tasks being performed autonomously (e.g., automated tasks 47235) and more tasks being performed manually (e.g., manual tasks 472401. For example, as shown in FIG. 11, when the surgical instrument is in autonomy level 2 47230, it may perform clamping autonomously and may result in the surgeon manually performing firing, stapling, positioning, and orientation. The update to the level of autonomy may be sent to the databased as described with respect to FIG. 9.

Figure 12:
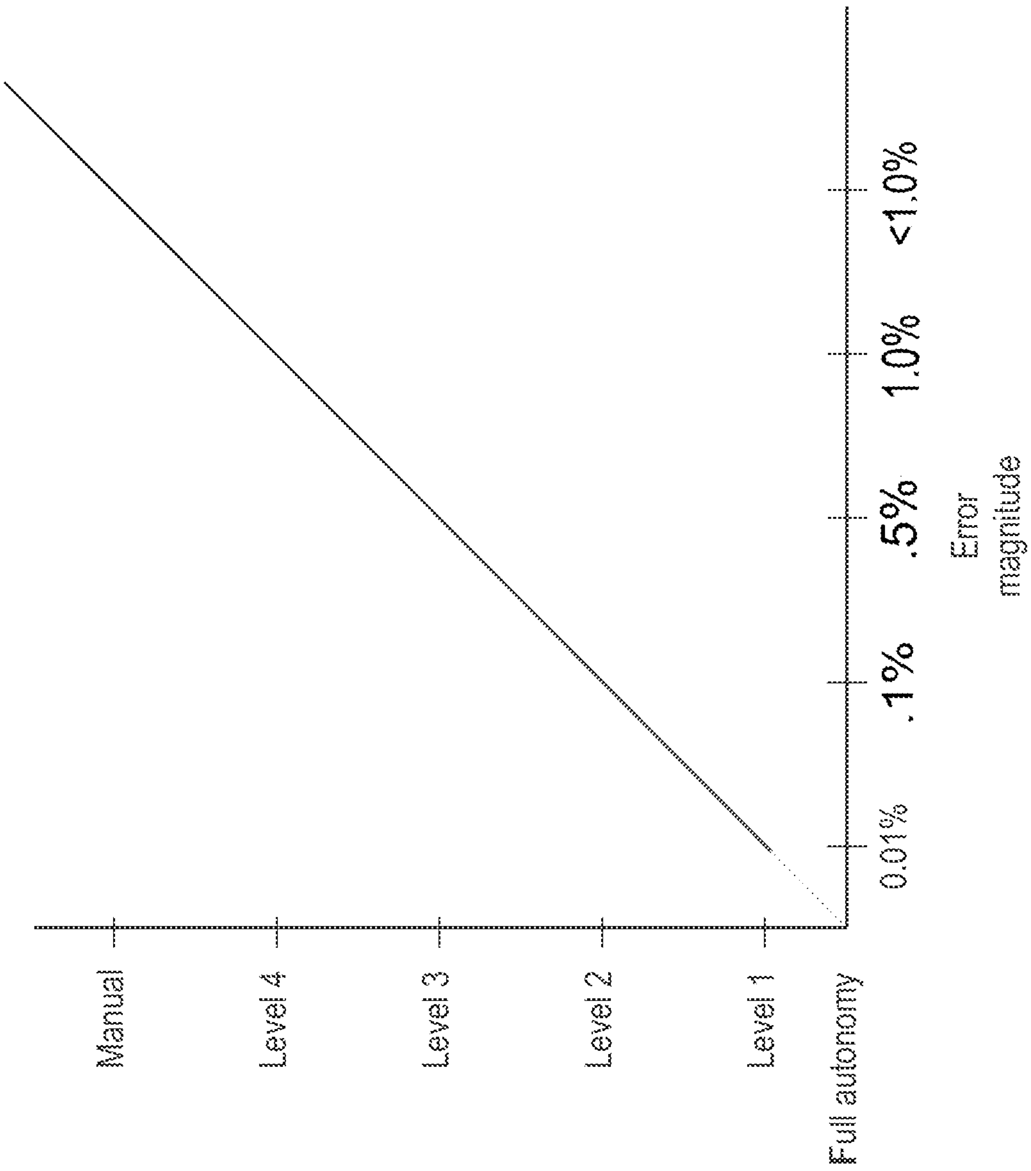
FIG. 12 shows an example of the relationship between error magnitude and autonomy levels.

FIG. 12 shows an example of the relationship 47245 between error magnitude and autonomy levels. In examples, an error magnitude may be associated (e.g., linked) with respective autonomy levels. The error magnitude may be used as the threshold described with respect to FIG. 11. For example, the monitoring module, described with respect to FIG. 11, may produce an output (e.g., delta output) based on the difference between measured conditions and ideal conditions. The output may be compared to the error magnitude (e.g., used as the threshold) to determine whether the current autonomy level is leading to an acceptable outcome. For example, as shown in FIG. 12, autonomy level 1 may be associated with error magnitude 0.01%. If the output, e.g., which may be a numerical value, from the monitoring module exceeds 0.010, an indication may be sent to the surgical instrument to switch the autonomy level, for example, to autonomy level 2.

As shown in FIG. 12, the error magnitude may increase as the autonomy levels increase, where an increased autonomy level has less tasks performed autonomously as described with respect to FIG. 9. If the autonomy level is switched, an indication may be sent to the monitoring module about the switch and the indication may include an updated error magnitude. For example, if the autonomy level is switched to autonomy level 2, an error magnitude of 0.1% may be sent to the monitoring module. The monitoring module may include a database, for example, the database described with respect to FIGS. 9 and 11. The monitoring module may send a message to the database to update both the current level of autonomy at which a surgical instrument is operating and the error magnitude value associated with the updated level of autonomy. The monitoring module may infer the level of autonomy based on the error magnitude.

The error magnitude associated an autonomy level may be determined. For example, the surgical hub may determine the error magnitude for an autonomy level based on historical data. The historical data may show a correlation between the likelihood of a poor outcome occurring and the error magnitude. The historical data may be based on an analysis of what happened when autonomous functions (e.g., associated with autonomy levels) were used to perform the capability in the past. The surgical hub may include an error magnitude module that calculates, based on the historical data, an error magnitude that minimizes the likelihood of a poor outcome occurring. In examples, the error magnitude module may determine the error magnitude based on weighing the benefits of performing a capability with an autonomous level versus performing the capability manually. For example, performing the capability manually may result in a likelihood of a poor outcome, which the error magnitude module may consider when determining the error magnitude. An indication of the error magnitudes may be sent to the monitoring module as described with respect to FIG. 11.

The error magnitudes associated with respective autonomy levels may be dynamic. For example, the surgical hub may send a range of acceptable error magnitudes for an autonomy level to the monitoring module. As the surgical instalment is performing the capability, surgical context data may be sent to the monitoring module, for example, from the surgical hub, the surgical instrument, or other devices associated with the surgery (e.g., wearables that the surgeon may be wearing). The monitoring module may send an indication to adjust the error magnitude based on the surgical context data. For example, the surgical context data may indicate that a critical step of the surgery is being performed. The monitoring module may obtain the data and send an indication to decrease the error magnitude (e.g., the decrease resulting in the threshold being crossed with fewer errors being made).

Figure 13:
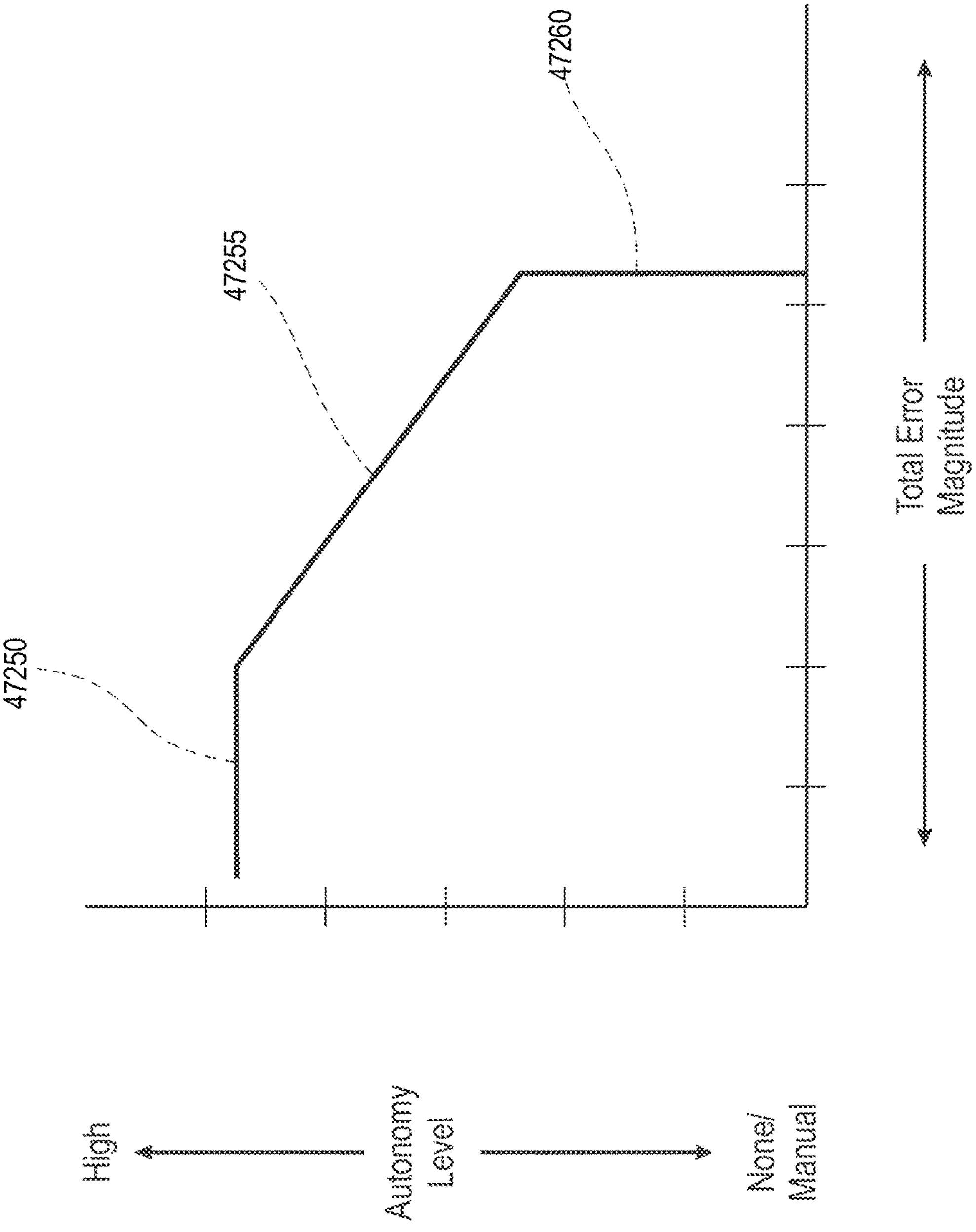
FIG. 13 shows an example of the relationship between error magnitude and autonomy levels.

FIG. 13 shows an example of the relationship between error magnitude and autonomy levels.

As shown in FIG. 13 a high level of autonomy 47250 (e.g., which results in a high number of tasks associated with the surgical instrument capability being performed autonomously) may be associated with a low error magnitude (e.g., total error magnitude). In examples, a high level of autonomy 47250 may be represented as autonomy level 1 as described herein. A low level 47260 of autonomy (e.g., which results in a low number of tasks associated with the surgical instrument capability being performed autonomously) may be associated with a high error magnitude (e.g., total error magnitude). As described with respect to FIG. 12, the error magnitude may be related to the threshold, which is used to determined if the autonomy level at which the surgical instrument is operating is to be switched.

As described with respect to FIGS. 12 and 9, the error magnitude may be determined based on historical data, surgical context (e.g., which may include environment data such as number of staff members in the surgical operating room (OR), surgical instrument data as described with respect to FIG. 11, and/or the like). The error magnitude may be determined based on the surgical tasks being performed autonomously. For example, an endocutter's capability may be resecting tissue. It May be set to autonomy level 1 to perform this capability, which may result in the surgical tasks of controlling the energy source, cutting, stapling, knob orientation, body orientation, body position, anvil jaw force, and reload alignment slot management (e.g., which are the tasks associated with resecting tissue) being performed autonomously. Data related to one or more of these surgical tasks, for example, knob orientation, may be obtained by the surgical hub and the surgical hub may use this data when determining the error magnitude. For example, the data may indicate that knob orientation is a task that is likely to be performed successfully when done autonomously. In such a case, the surgical hub may determine a low error magnitude. In examples, the error magnitude may be sent to a monitoring module, as described with respect to FIG. 12, and the monitoring module may infer the autonomy level being using by the instrument. The data may indicate that stapling is a task that is unlikely to be performed successfully when done autonomously. In such a case, the surgical hub may determine a high error magnitude. Data related to multiple tasks may be used, e.g., by the surgical hub, to determine the error magnitude. For example, both data from the knob orientation and data from the stapling may be sent to the surgical hub. The surgical hub may weigh both sets of data and determine a medium level of autonomy 47255 to be used, e.g., since the knob orientation a task that is likely to be performed successfully when done autonomously and stapling is a task that is unlikely to be performed successfully when done autonomously. Error magnitude may be determined for each task associated with the capability to be performed. For example, a surgical hub may determine knob orientation error magnitude, which may be used when assessing whether the autonomy level associated with knob orientation is to be switched as described with the respect to FIG. 12 and stapling error magnitude, which may be used when assessing whether the autonomy level associated with stapling is to be switched.

Figure 14:
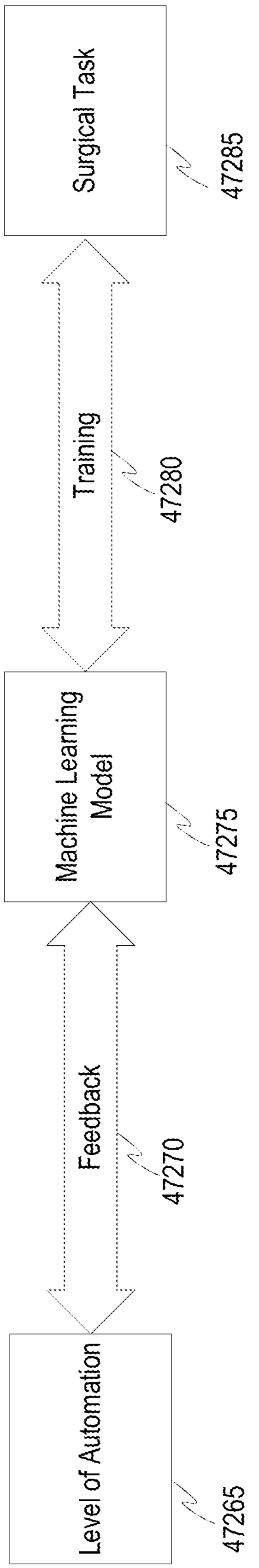
FIG. 14 shows an example of the relationship between autonomy level, machine learning, and the surgical task.

FIG. 14 shows an example of the relationship between autonomy level, machine learning, and the surgical task. Autonomy level and automation level may be used interchangeably herein.

As described herein, performing a surgical task:, associated with a surgical instrument capability, autonomously may involve using a machine learning framework. Machine learning framework is described in greater detail under the heading "Method for Surgical Simulation" in U.S. patent application Ser. No. 17/332,593, filed May 27, 2021, the disclosure of which is herein incorporated by reference in its entirety. For example, inputs (e.g., parameters) associated with the surgical task may be sent to a machine learning model 47275 and the machine learning model may be trained 47280 to perform the surgical task 47285 autonomously. The machine learning model 47275 may be involved in determining the level of autonomy 47265 that the surgical task 47285 should be performed at (e.g., autonomy level 1). Data related to the level of autonomy 47265 may be generated and sent to the machine learning model 47275 in the form of feedback 47270, where the model 47275 may adjust the input(s) associated with the surgical task 47285 and/or change the level of autonomy 47265 at which the surgical instrument 47285 is operating. The machine learning model 47275 may be located locally (e.g., a module on the surgical instrument or on a remote device.

Dynamic variables associated with performing the surgical task 47285 autonomously may be updated by a machine learning algorithm based on performance metrics as described with respect to FIG. 11. For example, the autonomy level 47265 associated with the surgical task 47285 may be updated based on an error magnitude (e.g., threshold) being crossed as described with respect to FIG. 12. The machine learn g model 47275 may use real-world data sets of previous surgeries when determining whether the error magnitude has been crossed and/or when determining the autonomy level 47265 associated with the surgical task 47285. The real-world data sets of previous surgeries may be an aggregation of the procedures done by a surgeon, the surgeries from that facility and; a compilation of surgeries using hubs within the same network.

The machine learning algorithm may be updated by data from a cloud and/or remote system, for example, which may be compiling best practices, regional data on surgeries, and/or worldwide outcomes and step-of-use from any number of other facilities worldwide.

The real-world information may be derived from procedure outcomes, for example, from. the region, population etc. and/or may be interpolation and/or aggregation of sub-biomarker measures and outcomes.

For example, a machine learning model 47275 based on GANs (GANs model) may be trained using past surgical procedure data. The GANs model may model that data pattern that given a surgical step, a list surgical tasks 47285 may be performed autonomously. The GANs model may model the probability distribution of the surgical tasks 47285 present in the past surgical procedure data. Thai: is, when the GANs model generates a surgical task 47285 from the list of possible surgical tasks 47285, the surgical task 47285 is generated at a probability according to the probability distribution.

Machine learning may be a part of a technology platform called cognitive computing (CC), which may constitute various disciplines such as computer science and cognitive science. CC systems may be capable of learning at scale, reasoning with purpose, and interacting with humans naturally. A CC system may be capable of performing surgical tasks autonomously.

The output of machine learning's training 47280 process may be a model 47275 for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model 47275 the training 47280 process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic Sanctions. The NN algorithm may include a cost function to minimize classification errors by adjusting, the biases and weights through a process of feedforward propagation and backward propagation. When a global minimum may be reached, the optimized hypothesis function with its layers of adjusted biases and weights may be deemed trained and constitute the model 47275 the training process 47280 has produced.

Figure 15:
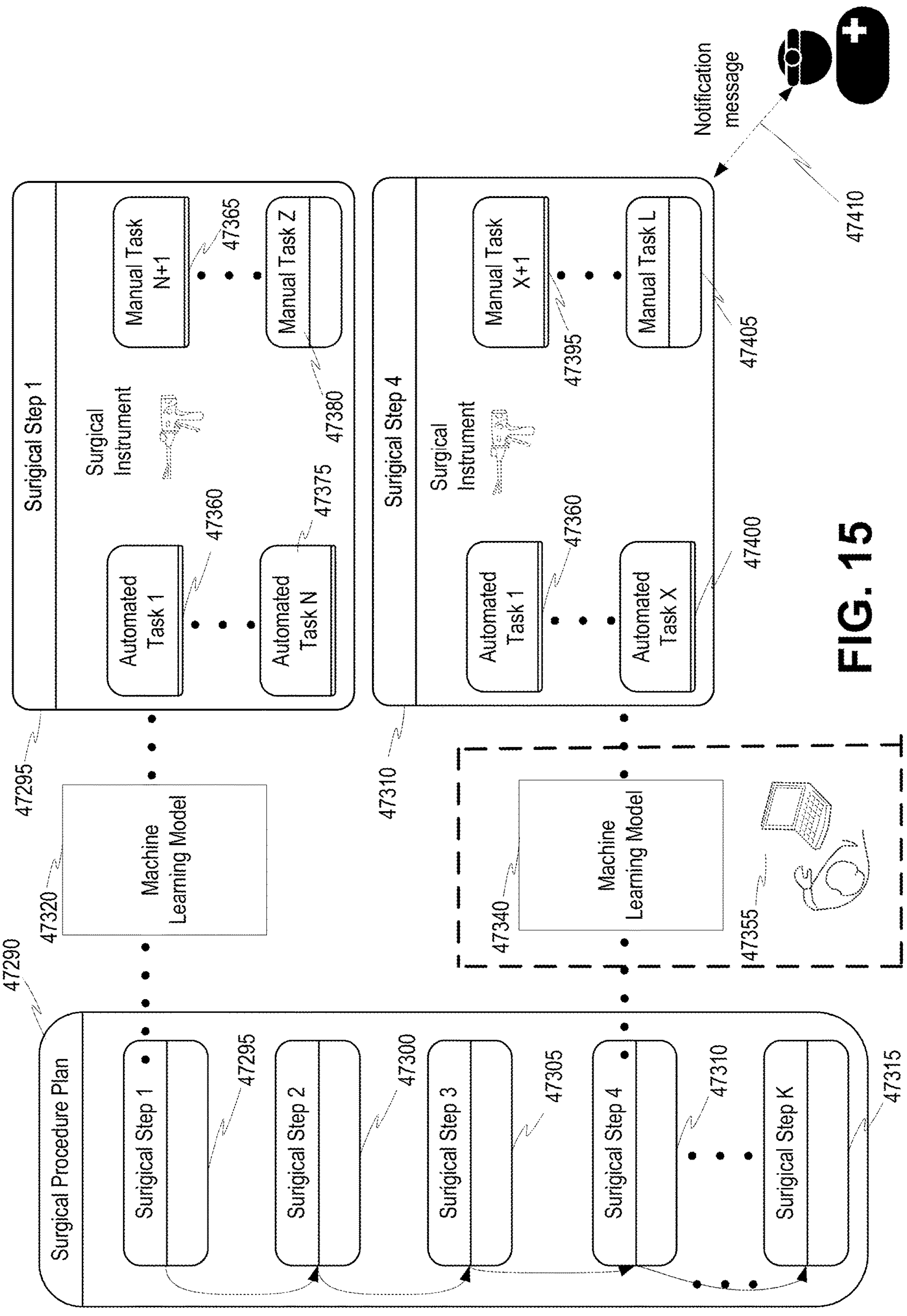
FIG. 15 shows an example determining the autonomy levels at which the surgical instrument performs a surgical task.

FIG. 15 shows an example determining the autonomy levels at which the surgical instrument performs a surgical task. As described with respect to FIG. 9, the surgical task(s) may be associated with a capability of the surgical instrument, for example, tissue resection. The surgical steps may be associated with the capabilities.

A surgery may follow a surgical procedure plan 47290 which may outline surgical steps to be performed (e.g., surgical step 1 47295, surgical step 2 47300, surgical step 3 47305, surgical step 4 47310, and surgical step K 47315). The surgical steps may be performed in sequence. In examples, the surgical steps may be performed in parallel. A surgical hub or other device may obtain the name of the surgery to be performed and generate the surgical procedure plan based on historical data related to the success of pervious surgeries or previous simulations of the surgery (e.g., performed at a facility). The surgical hub may consider data (e.g., additional data) when generating the surgical procedure plan such as the experience level of the surgeon.

One or more surgical steps (e.g., each surgical step) may include surgical task(s) to be performed by a surgical instrument. As described with respect to FIG. 11, one or more of the tasks may be performed autonomously and one or more may be performed manually, which may be determined based on the autonomy level associated with the capability (e.g., surgical step). In examples, all the surgical tasks may be performed autonomously, for example, if the capability is associated with the highest autonomy level (e.g., "full autonomy" level as shown in FIG. 12).

A machine learning model may be used in determining the autonomy level for a surgical step (e.g., machine learning model 47320 associated with surgical step 1 47295 and machine learning model 47340 associated with surgical step 4), as described with respect to FIG. 14. In examples, parameters for the machine learning model may be entered by a user 47355. The machine learning model 47320 may output that for surgical step 1 47295, tasks 1 47360 to N 47375 are to be performed autonomously and tasks N+1 47365 to Z 47380 are to be performed manually (e.g., by the surgeon or another surgical staff member). machine learning framework may receive feedback about the performance of the surgical step. If the performance crosses a threshold, the machine learning model may obtain a message that the autonomy level is to be switched. In such a case, the model may determine an updated autonomy level based on the feedback about the performance of the surgical step, which may include one or more of real-time surgical data, user data, surgical environment data, surgical instrument data, task data, or historical data. The update may occur during the surgical step. The update may occur based on the transition from one surgical step to another surgical step (e.g., during the transition from surgical step 1 to surgical step 2). The updated autonomy level may be associated with a different set of surgical tasks to automate (e.g., perform autonomously). For example, based on the transition to surgical step 4 47310, the tasks 1 47360 to X 47400 may be performed autonomously and tasks X+1 47395 to L 47405 may be performed manually. A message 47410 (e.g., a simple notification service (SNS)) may be sent to the surgeon or other surgical staff member of the updated autonomy level. The surgical tasks to be performed autonomously and manually may be sent via the message.

Figure 16:
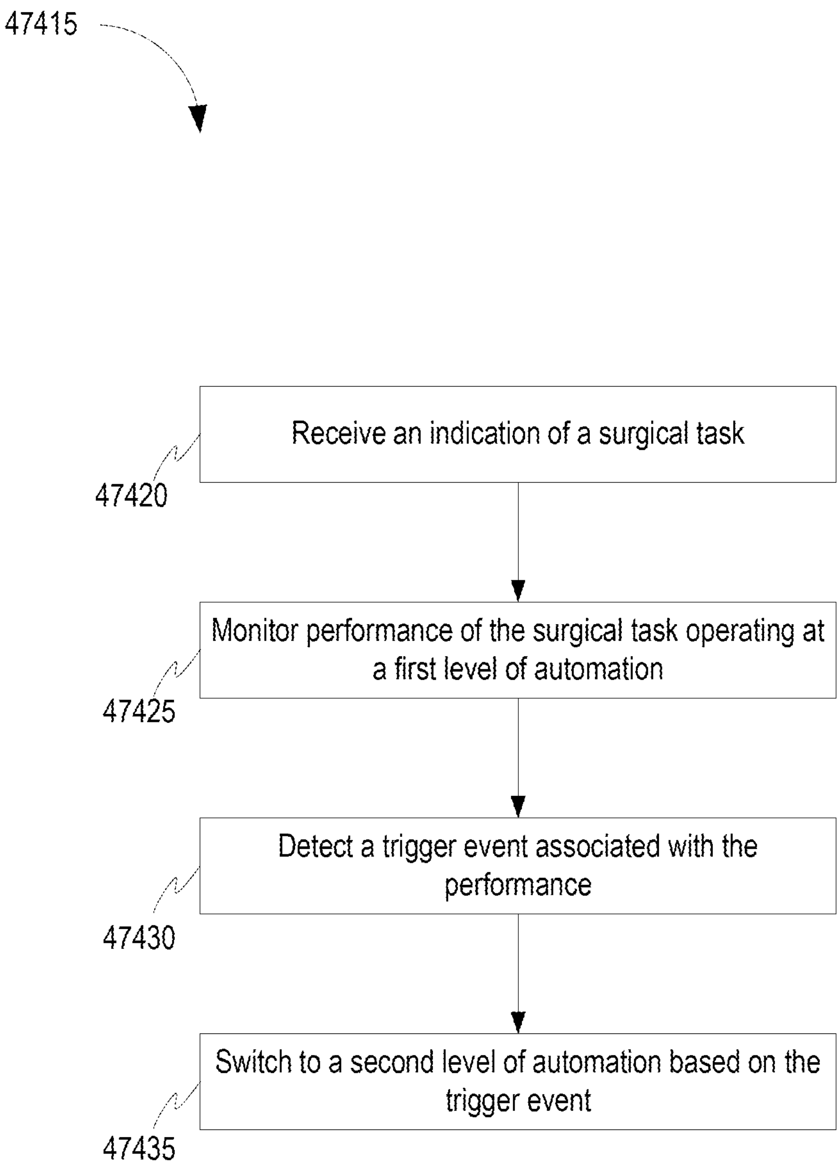
FIG. 16 shows an example flow chart for automating surgical tasks associated with autonomy levels.

FIG. 16 shows an example flow chart 47415 for automating surgical tasks associated with autonomy levels. At 47420, the device may receive an indication of a surgical task to be performed with a surgical instrument. Capabilities of the surgical instrument may be associated with levels of automation.

At 47425, the device may monitor a performance of the surgical task with the surgical instrument operating at a first level of automation associated with the levels of automation. The capabilities of tile surgical instrument may include a set of surgical instrument tasks and the level of automation may be associated with automating one or more surgical instrument tasks from the set of surgical instrument tasks.

At 47430, the device may detect a trigger event associated with the performance of the surgical task and switch operation of the surgical is from the first level of automation to a second level of automation associated with levels of automation, for example, based on the trigger event. The performance of the surgical task may be based on real-time surgical data. The real-time surgical data may include one or more of the following: user data, surgical environment data, surgical instrument data, task data, historical data, or the like.

At 47435, the device may detect the trigger event by comparing the performance of the surgical task with a trigger event threshold and may switch operation of the surgical instrument from the first level of automation to the second level of automation based on the trigger event. The second level of automation may be associated with automating less surgical instrument w tasks hen compared to the first level of automation. Monitoring the performance of the surgical task may include comparing one or more of the real-time surgical data to respective ideal surgical data.

In examples, the device may operate at a first level of automation of the levels of automation associated with the surgical task. The device may obtain an indication to switch to a second level of automation of the levels of automation associated with the surgical task. The indication may be based on detecting a trigger. The device may operate at the second level of automation of the levels of automation associated with the surgical task based on the indication. The indication may be based on monitoring a performance of the first level of automation. The performance of the first level of automation may be based on real-time surgical data.

Autonomous decision-making and assisting may be provided. Auto-determination of the level of autonomy (e.g., level of automation) from a predefined set of options may be based on identifying the situation (e.g., using situation awareness) of the surgical task.

Smart medical device determination of the level of automation may be based on the monitored situation of the procedure. For example, a powered adaptable medical device control algorithm for controlling a medical instrument function may include a variable magnitude of automation. Monitoring of the instrument, surgeon, and/or patient may control the magnitude or level of automation (e.g., the control algorithm) without direct user control. In examples, the level of automation may be based on one or more of the following: the capabilities of the device, the connections of the device to other devices, the presence of a number of personnel, or detection of an aspect of its status and/or configuration.

Automated task categorization (e.g., selectable set of choices that are available) may be requested by the surgical instrument (e.g., a request message may be sent to the surgical hub) and an assessment of the complexity may be used to automatically determine the level of appropriate automation for the surgical instrument, e.g., in order to perform the surgical task.

Features describe herein may result in more autonomy. For example, there may be a release from automated operation based on product in-servicing. The level of autonomy may be determined based on user (e.g., surgeon) skill level. For example, inexperienced users (e.g., resident surgeon) may trigger a lower level of automation to be used, e.g., to ensure proper operation of the surgical instrument. For example, an inexperienced user (e.g., resident surgeon) may have to pull an endocutter in an emergency situation of the surgical task. The surgical hub and/or surgical instrument may recognizes that the skill level of the user as inexperienced (e.g., novel) and may set automation to minimize choices and maximize easy-of-use with limited user control activations. An autonomy level may be associated with user selectable options and, if an inexperienced user may have less selectable options than an experienced user (e.g., the selectable options are locked-out and automatically grayed-out). More advanced users may be given an option to automate more (e.g., surgical tasks which results from using a higher level of automation) than inexperience users.

The level of autonomy may be based on a user field of view. For example, if the surgical move outside the field of view (e.g., laparoscopic field of view), an autonomous instrument control may be adjusted. For example, during surgery the surgeon may have multiple ports link to multiple different instruments to perform the intended task and may have one laparoscopic camera with a restricted/defined view. Throughout the surgery, the surgeon may switch between instruments and/or move instruments to increase access. In such a case, one or more of the instruments may no longer be in the field of view. The instrument may activate an autonomous mode in which the device function may not be activated until it is moved back into the field view.

Device (e.g., surgical instrument orientation may be autonomously controlled. For example, if the instrument is outside the field of view and the surgeon attempts to place the instrument back into the field of view, the device end effector may autonomously control itself in which it may rotate and/or orient itself to not contact other structures/tissue/organs until it was back into the field of view, which may prevent unintended actions.

Autonomous instrument control may be based on the surgeon's focus or viewing angle which may be fixated on a portion of the screen. For example, during surgery, the surgeon may be viewing from a laparoscopic camera. The surgeon may get disoriented and/or fixated on a certain task of function (e.g., while mobilization or creating access to the targeted site, his/her focus may be fixated on a portion of the screen). In such a case, the surgical instrument may switch to an autonomous mode that would limit certain functions until the surgeon's eyes were redirected to that instrument. In such case, instruments ins determine an autonomous mode that may result in no contact to other structures. For example, the autonomous mode may allow the end effector to move or orient autonomously as the surgeon translates the device into the focus area of the screen.

The facility operators and/or surgeon may choose to limit autonomy customization based on risk level. The level of autonomy to assist in surgery may be set/controlled (e.g., preemptively). For example, this may be based on administrative approval, safety concerns and/or risk to patients. The facility operators may choose to use the default automation, which may enable more inexperienced surgeons to get more repeatable results. The facility operators may choose to disable or deactivate available levels of autonomous operation, e.g., until it validates the behavior aligns with their approach to surgical intervention and/or outcomes. This may prevent devices from being brought into the facility and causing poor outcomes because the autonomous function that was used was incompatible.

Adjusting the autonomy level may be based on task and/or patient risk. Laparoscopic ultrasonic devices may have multifunctional uses such as one or more of the following: coagulation, cutting, dissecting, or grasping. Based on the intended function, targeted zone, and/or surgical task, the autonomy level may be controlled by the intended function and/or patient risk, for example, to control the allowed operations by the autonomous system and/or the combination of human activation. In examples, the higher the risk to the patient may transfer the execution of a task from an autonomous state to a mixed state with the surgeon having to approve an action before it is performed since the action may result in a greater negative outcome to the patient. In such a case, the surgeon may be prepared to react if an unintended outcome occurs (e.g., computer-controlled systems may have more precise controls, however humans/surgeons may anticipate issues and adjust their response to complete the task). For example, the patient risk may be level 1. The surgical instrument may be used for grasping and tissue manipulation. Based on the level 1 risk, the surgical instrument may allow for full autonomy of the jaws opening and closing. For example, the patient risk may be level 2. The surgical instrument may be used for cutting and dissecting. Based on the level 2 risk, the surgical instrument may allow full autonomy of the jaws and energy activation when on non-vascular tissue but may not on fatty tissue. In examples, the patient risk level may be 3. The surgical instrument may be used for vessel sealing and/or coagulation. Based on the level 3 risk level, the surgical instrument may allow full autonomy of the jaws but energy activation may be controlled/applied by the surgeon. This may result in less automation and more discrete operation. The autonomy level may be based on procedure complexity and/or patient specific implications (e.g., co-morbidities). The autonomy level may be based on detected issues.

The facility may limit devices automation (e.g., level of automation) of processes, e.g., until the facility has validation of use (e.g., the device function are intended and are cost beneficial).

An autonomy level may be based (e.g., switched based on) safety risk, incorrect operation of surgical instrument, and/or detected issue with surgical instrument. For example, safety energy activation may be used. For ultrasonic and/or RF energy devices, keeping the jaws and active electrodes clean and free of debris throughout the procedure may prevent tissue build-up which may lead to unintended generator errors and/or reduction in performance. To complete a task, the surgeon may remove the device from the patient and the surgeon and/or scrub nurse may use a sponge to clean the jaws. As a safety precaution, the device may autonomously activate a safety mode when sensed that the jaws be cleaned to ensure energy activation may not be activated while cleaning. In examples, for harmonic devices, if the blade is accidentally activated while using hemostasis while cleaning the blade and/or the blade makes contact with something while cleaning and in motion back to the patient, this may lead to scratches, nicks and/or notches in the blade which may increase the potential for premature blade failures. Having the power autonomously deactivated while not in the patient may minimize these issues. For example, safety jaw closure may be used. For surgical procedures, devices with end effectors may be closed while passing through the trocar. Autonomously, the devices may close the jaws prior to being removed or inserted into the trocar. Thermal damage may be used. Energy devices like the Harmonic Scalpel (e.g., ACE Family) may reach temperatures in excess of 200° C. while performing the intended task, or after deactivation of the energy button. These devices may take longer to cool. Autonomously, the system may control the allowable movement of the jaws and/or restrict movement until an acceptable temperature of the jaws is met to ensure adjacent tissue is not inadvertently impacted by thermal damage.

Having selectable levels of automation may result in more or less autonomy based on the setting and/or options available facility operators and/or user may use more advanced features (e.g., associated with higher level of autonomy) in a certain setting. For example, smart software modules, more comprehensive control programs, and/or capacity of the hardware may be used to determine the level of autonomy. The user of the more advanced functions may select a more constrained level of autonomy based on their needs (e.g., a teaching facility may use higher levels of autonomy to ensure safety of less experienced surgeons or a regional facility may deactivate an autonomous function because in that region it is seen as not benefiting the patient or it may cause more challenges than it solves).

A tiered approach may be used to assess risks associated with a surgical task, which may include one or more of the following: accept risk, avoid risk, transfer risk, or reduce risk.

A device may be identified within a larger digital ecosystem. The device may be detected other systems that are capable of integration or intercommunicating with the device and/or system.

The autonomy level may be based on the presence of cooperative devices or systems. For example, a first smart device may detect the presence of a second smart device or surgical hub which may initiate automated communication interaction. Once the smart devices are communicating, the type and/or configuration of the second smart hub may enable the automated update or communication of operational parameters for the first device that may enable an updating of the system. Once the first device is operated, it may automatically update the second smart Hub with the information regarding its use which may be in-turn automatically compiled with other information from other devices and automatically parsed and disseminated to other systems that use some portion of that data.

This distributed data may be used when determining the level of autonomy for the surgical instrument within the cooperative system. Product detections may be used as a trigger to perform the features described herein. For example, one or more of the following may be a trigger: the presence of a smart device in a smart hub proximity; the presence of a smart component within a smart device (e.g., RFID within a smart staples); the presence or proximity of cooperative compatible devices (e.g., smart proximity sensing scope or scope add-on and the presence of a smart device with integrated fiducial markers); a first hub within range of a second hub, smart OR, network gateway, and/or communication backplane generator; or a first imaging system within range of a second imaging system.

The system's ability to measure and/or detect the information to operate at a level of autonomy may be determined.

HCPs within the room capable of interacting or operating with the device may be determined. For example, the adequate number of appropriate users may be determined, which may include one or more of the following area of expertise and/or job function (e.g., surgeon, anesthesiologist, scrub tech, circulator nurses, etc.); experience level (e.g., overall time within medical field, time/quantity of work within given specialty, time/quantity of work within given a procedure, time/quantity of work with specific equipment, and/or certifications and training); skill level (e.g., detected by previous operations, device usage, outcomes, etc.); or manually inputted into the system by users/management. One or more of the following may be used to determine who is in the room: manual input; manual badge scanner; room badger scanner (e.g., auto-check and update who is present in room); facial recognition, or the like.

The autonomy level may be based on one Or more of the following: are there insufficient number of people in the room which defaults to automated operation by a limited number of users. For example, if an insufficient number of staff are present, a level of automation may be determined (e.g., adjusted to complete the procedure. In examples, the procedure (e.g., tasks of the procedure) may be updated, which may result in greater efficiency as automation increases by the adjustments.

Notification of the reasoning why a certain automation level has been selected may be provided, which may be used to change selection criteria to be used when selection the automation level. Users may be informed of variables that are affecting the level of automation. For example, if there are insufficient personnel in the room, the surgical instrument: may default to manual operation (e.g., or default to autonomous).

Determination of the triggers and/or the magnitude of the autonomy may be based on monitored and/or calculated data feeds. During the performance of a task being. performed autonomously, there may be a no good autonomy level options. In such a case, it may be determined how to adjust its level of autonomy. For example, it may be determined to change from one autonomy to a lower level autonomously safely. In examples, it may be determined to finish the current task and stop (e.g., do not proceed the next task. In examples, it may be determined to terminate immediately.

The detected magnitude of error in the information may be used as a means to determine a level of autonomy. For example, as the level of error increases, the level of autonomy decreases. The magnitude of error may include a system-based cumulative total error and/or the criticality of a single error. In examples, a single error with a high degree of criticality may reduce the autonomy of the system more than multiple errors of small or insignificant magnitude. There may be errors which partially remove autonomy of the system. For example, a highly autonomous equipment system such as a surgical robot may have multiple arms connected to it. During a start up test sequence, one of the arms may be detected to have an error with it's feedback sensor based on output data and feedback. It may be determined that a feature of the arm is not operating correctly. The system may eliminate autonomy activity for that arm, while maintaining autonomous activities with other arms. There may be errors which completely remove autonomy of the system. For example, a highly autonomous equipment system such as a surgical robot may use a mainframe processing location. While redundancies exist with certain aspects (e.g., power supplies), there may be no redundancy for the central processor if there is a failure of the processor, all autonomy for the system may be removed. There may be errors that have no impact on the level of autonomy of the system. For example, a highly autonomous system such as a surgical robot may rely on a GPS signal to calculate time and date, as well as country of location, for record keeping. That GPS signal may become lost and may create an error. There may a holdover period for 24 hours from which prior data is still deemed accurate. In such a case, although an error has occurred, there may be no impact to functionality or autonomy level.

In examples, true cumulative error may not be calculated. In such a case, specific functions and features related to autonomy may be removed dependent upon the associated failure mode. Each potential autonomous function of the device may be mapped to one or more corresponding physical/software functions of the device.

User controlled input actuator may be provided. An autonomy kill switch may include one or more of the following: button that removes all autonomy from the system, e.g., regardless of the current step or state the system; button that removes autonomy from the system, e.g., after it has completed it's current activity; multiple state button (e.g., state one for the button allows autonomy to finish it's current activities and state two for the button removes all autonomy immediately regardless of current activities); or configurable Button (e.g., the button may be configured for how it should operate such as removal of autonomy immediately or at completion of activities).

Sensed event related to the device may be used, which may include one or more of the following energy events: initial sensed force contact, rate of force increase, impendence thresholds, thermal spread/damage, or jaw temperature. For example, as the jaws are closed, the first holing that the current through the motor may be sensed and may be used to determine tissue height. If that was determined thick for the end-effector, the motor speed may be changed based on that threshold. Triggers may be used to cause alteration to autonomy. For example, a too thick condition may cause the device to stop automation and request user input.

Impedance may be used as a trigger. For example, when energy activated within the jaws, the generator may monitor the impedance of the tissue and/or vessel to determine when energy should be turned off. A product code may be indicated for a maximum vessel sealing size (e.g., typical ≤5 mm or ≤7 mm size). An energy algorithm may account for impedance over time. If the energy activation cycle was too short compared to a normal cycle, this may indicate and/or signal damaged and/or diseased tissue and indicate/notify the user to take over activation control. If the energy activation cycle was longer compared to a normal cycle, this may indicate and/or signal that tissue is fatty and/or is a larger vessel size than the product is indicated for an may transfer responsibility to the surgeon. Built-up tissue on the jaws may alter the impedance control. When this condition occurs based on calculated time verse actual, it may notify the user to clean the jaws. In examples, a harmonic 7 may be operated at a power level 3 only for vessels ≤5 mm in diameter and an advance hemostasis mode for vessel sizes ≤7 mm. In such a case, the system may autonomously select/alter the power level based on identified vessel size. When a vessel is above or between sizes, the system may request from the user which power level to proceed with.

Thermal spread may be used as a trigger. During energy activation and vessel sealing, criteria that may be monitored along with hemostasis is thermal damage and/or thermal spread. Temperature and/or lateral thermal damage may be considerations for surgeons when using energy-based technologies. Surgeons may be concerned about injury to nearby structures either by direct contact or by the visually unrecognizable transmission of energy. Surgeons may be concerned about the potential impact of tissue damage on the inflammatory response and overall recovery of the patient. Monitoring thermal spread during energy activation, along with the tissue type, thickness, power level, and/or clamp pressure, may lead to calculating the actual verse nominal, which may be used to notify user to and/or to autonomously adjust power settings and/or clamp pressure (e.g., Harmonic ACE+7 2.54+/−0.48 mm, which refers to mean & std. deviation). Preclinical comparisons of caprine vessel sealing may be used when autonomously adjusting. Thermal damage may result from the generation of heat by an advanced energy device and may be a critical component to vessel sealing and/or tissue transection. The temperature the is reaches may be dependent on multiple variables, including tissue type, tissue thickness, energy used, and/ power setting. An advanced energy devices may reach instrument temperatures of at least 100° C. during activation on tissue. There may be situations when the temperature of an ultrasonic device may reach beyond the 100° C. range due to tissue conditions. When jaws reach this temperature, the surgeon may unintentionally make contact with unintended tissue and cause trauma. When this occurs, this may trigger a wait time until the jaw temperature is reduced to an acceptable temperature. In such a case, if it made contact with tissue no trauma would occur or if the surgeon attempts to move the device, the autonomy control may take over the finite control (e.g., if the surgeon moved the device distal with a fast and/or larger motion than allowed, the autonomy may slow down and/or reduce the displacement to ensure the high temperature jaws may not make contact with the tissue and/or unintended treatment area).

Stapling device may be used as trigger. For example, an unanticipated articulation force may be used.

Automatic risk determination level may be provided. User choices may be compared to a benchmark on other facility users or a global user choice level to determine permission level associated with autonomy level. Active surgeon choices may be monitored control the autonomous choices. Setting uncertainty level or pre-selected user risk level may be used to determine acceptable risk level in its decisions. Previous operations or outcomes may be used to determine what the effective risk level may be.

Risk: matrices for a system to use to determine appropriate risk may be provided. The matrices may include medical or patient (e.g., Claims History such as International Classification of Diseases. Tenth Revision, Clinical Modification (ICD010-CM), hierarchical condition category (HCC), electronic health records ('HER-health information technology (HIT) database and/or the like).

The overall risk determination may be a combination of the risks associated the patient, device and procedure.

Adjustment of the level of autonomous function may be based on historic user control, previous autonomous operation, and; historic outcomes resulting from previous autonomous determination. Autonomous failures and/or user overrides/assistance may reduce the level of autonomy and/or the frequency of suggested autonomous operation. Undesirable outcomes may adjust the level of autonomous engagement (e.g., if user errors caused it, less autonomous engagement when compared to if autonomous operation caused it). Historic user interactions that resulted in confusion, misuse, or instructions for use issues may result in the system assisting with autonomous prompting and/or control to minimize future issues with use, for example, delay of procedure counting.

Aggregation of data may be utilized to adjust autonomy levels. For example, weighted comparison of deciding how to react to historic information may be used. Criticality of the failure, local frequency, uniqueness of the failure, etc. may be used. Uniqueness may include compete motor failure and/or complete reset of the system (e.g., RF interference with the system operation resulting in a complete restart to continue use).

The invention claimed is:

1. A device for automating a surgical task, the device comprising:

a processor configured to:

receive an indication of the surgical task to be performed with a surgical instrument, wherein capabilities of the surgical instrument are associated with a first level of automation and a second level of automation;

monitor performance of the surgical task with the surgical instrument operating at a first level of automation;

determine a first error magnitude based on the performance of the surgical task with the surgical instrument operating at the first level of automation and based on a number of health-care professionals in an operating room during performance of the surgical task;

determine a second error magnitude based on a historical performance of the surgical task with the surgical instrument operating at the second level of automation and based on the number of health-care professionals in the operating room during performance of the surgical task;

detect a trigger event based on the first error magnitude, the second error magnitude, and the number of health-care professionals in the operating room during the performance of the surgical task, wherein the trigger event indicates that the performance of the surgical task has degraded relative to the historical performance of the surgical task;

based on the trigger event, switch operation of the surgical instrument from the first level of automation to the second level of automation;

cause the surgical instrument to perform at least one surgical task autonomously based on the second level of automation thatis not performed autonomously by the surgical instrument based on the first level of automation; and in response to the switching operation of the surgical instrument from the first level of automation to the second level of automation, send an indication to a display that indicates that an insufficient number of health-care professionals are available during the performance of the surgical task.

2. The device of claim 1, wherein the capabilities of the surgical instrument comprise a set of surgical tasks, and wherein each level of automation of the first and second levels of automation is associated with automating one or more surgical tasks from the set of surgical tasks.

3. The device of claim 2, wherein the second level of automation is associated with zero manual input from a surgeon.

4. The device of claim 2, wherein the second level of automation is associated with a reduced manual input from a surgeon compared to the first level of automation.

5. The device of claim 2, wherein the trigger eventis associated with an impedance of a target tissue, and wherein the performance of the surgical task is associated with an application of energy to the target tissue via a set of jaws operated by the surgical instrument, and wherein the second level of automation is associated with automating less surgical tasks when compared to the first level of automation.

6. The device of claim 1, wherein the processor is further configured to:

send an indication to the display indicating the switched operation of the surgical instrument from the first level of automation to the second level of automation, wherein the indication of the switched operation comprises the at least one surgical task that is performed autonomously based on the second level of automation.

7. The device of claim 1, wherein the second level of automation is associated with higher manual input from a surgeon when compared to the first level of automation.

8. The device of claim 1, wherein the at least one surgical task that is performed autonomously reduces the first error magnitude.

9. A method for automating a surgical task, the method comprising:

receiving an indication of the surgical task to be performed with a surgical instrument, wherein capabilities of the surgical instrument are associated with a first level of automation and a second level of automation;

monitoringperformance of the surgical task with the surgical instrument operating at a first level of automation;

determining a first error magnitude based on the performance of the surgical task with the surgical instrument operating at the first level of automation and based on a number of health-care professionals in an operating room during performance of the surgical task;

determining a second error magnitude based on a historical performance of the surgical task with the surgical instrument operating at the second level of automation and based on the number of health-careprofessionals in the operatingroom duringperformance of the surgical task;

detecting a trigger event based on the first error magnitude, the second error magnitude, and a number of health-care professionals in an operating room during the performance of the surgical task, wherein the trigger event indicates that the performance of the surgical task has degraded relative to the historical performance of the surgical task;

based on the trigger event, switching operation of the surgical instrument from the first level of automation to the second level of automation;

causing the surgical instrument to perform at least one surgical task autonomously based on the second level of automation that is not performed autonomously by the surgical instrument based on the first level of automation; and in response to the switching operation of the surgical instrument from the first level of automation to the second level of automation, sending an indication to a display that indicates that an insufficient number of health-care professionals are available during the performance of the surgical task.

10. The method of claim 9, wherein the second level of automation is associated with zero manual input from a surgeon.

11. The method of claim 9, wherein the second level of automation is associated with a reduced manual input from a surgeon compared to the firstlevel of automation.

12. The method of claim 9, wherein the performance of the surgical task is based on real-time surgical data.

13. The method of claim 9, wherein the method further comprises:

sending an indication to a display indicating the switched operation of the surgical instrument from the first level of automation to the second level of automation, wherein the indication of the switched operation comprises the at least one surgical task that is performed autonomously based on the second level of automation.

14. The method of claim 9, wherein the trigger event is associated with an impedance of a target tissue, and wherein the performance of the surgical task is associated with an application of energy to the target tissue via a set of jaws operated by the surgical instrument, and wherein the second level of automation is associated with automating less surgical tasks when compared to the first level of automation.

15. The method of claim 9, wherein the second level of automation is associated with higher manual input from a surgeon when compared to the first level of automation.

16. The method of claim 9, wherein the at least one surgical task that is performed autonomously reduces the first error magnitude.

* * * * *